(12) United States Patent
Bielser et al.

(10) Patent No.: US 12,186,153 B2
(45) Date of Patent: Jan. 7, 2025

(54) AUTOMATED TOOTH ADMINISTRATION IN A DENTAL RESTORATION WORKFLOW

(71) Applicant: DENTSPLY SIRONA Inc., York, PA (US)

(72) Inventors: Daniel Bielser, Schaffhausen (CH); Sandro Löschhorn, Niederglatt (CH); Evgenij Derzapf, Lorsch (DE); Björn Steffen, Zurich (CH); Maryna Waszak, Oslo (NO); Philippe Widmer, Bern (CH)

(73) Assignee: Dentsply Sirona Inc., York, PA (US)

( * ) Notice: Subject to any disclaimer, the term of this patent is extended or adjusted under 35 U.S.C. 154(b) by 607 days.

(21) Appl. No.: 17/477,755

(22) Filed: Sep. 17, 2021

(65) Prior Publication Data

US 2023/0087800 A1    Mar. 23, 2023

(51) Int. Cl.
*A61C 7/00* (2006.01)
*G06N 20/00* (2019.01)
*G06T 19/20* (2011.01)

(52) U.S. Cl.
CPC ............. *A61C 7/002* (2013.01); *G06N 20/00* (2019.01); *G06T 19/20* (2013.01); *A61C 2007/004* (2013.01); *G06T 2210/41* (2013.01); *G06T 2219/2004* (2013.01)

(58) Field of Classification Search
None
See application file for complete search history.

(56) References Cited

U.S. PATENT DOCUMENTS

| 4,867,268 | A | 9/1989 | Ulert | |
|---|---|---|---|---|
| 5,428,193 | A | 6/1995 | Mandibert | |
| 5,921,941 | A | 7/1999 | Longobardo | |
| 8,051,946 | B1 | 11/2011 | Murad | |
| 2009/0017410 | A1* | 1/2009 | Raby | A61C 7/146 433/2 |
| 2010/0212995 | A1 | 8/2010 | Hmayakyan | |
| 2018/0206939 | A1* | 7/2018 | Kim | B33Y 80/00 |
| 2019/0231480 | A1* | 8/2019 | Moore, III | B33Y 80/00 |

FOREIGN PATENT DOCUMENTS

| EP | 2865337 A1 | 4/2015 |
|---|---|---|
| FR | 2766351 A1 | 1/1999 |
| WO | 2005030054 A1 | 4/2005 |
| WO | 2011097418 A2 | 8/2011 |

OTHER PUBLICATIONS

International Search Report; PCT/US2021/068074; Oct. 14, 2021 (completed); Oct. 25, 2021 (mailed).
Written Opinion of the International Searching Authority; PCT/US2021/068074; Oct. 14, 2021 (completed); Oct. 25, 2021 (mailed).

* cited by examiner

*Primary Examiner* — Frank S Chen
(74) *Attorney, Agent, or Firm* — SCHWEGMAN LUNBERG & WOESNNER, P.A.

(57) ABSTRACT

A method and system to automate an administration and restoration generation process that includes forming a spline along a jaw, proposing potential interdental gaps, weighting the potential interdental gaps to obtain one or more delimiters, automatically proposing tooth number probabilities, and computing a best fit tooth number distribution to generate a patient specific restoration.

33 Claims, 21 Drawing Sheets

AUTOMATED TOOTH ADMINISTRATION IN A DENTAL RESTORATION WORKFLOW

TECHNICAL FIELD

The present invention relates generally to a method, system, and computer program product for automated tooth administration in a dental workflow. More particularly, the present invention relates to a method, system, and computer program product for generating tooth restorations through an automation process that includes an automated administration phase.

BACKGROUND

Presently, technology exists to propose tooth restorations for dental professionals. For example, in a restoration workflow, 3D images of a patient's dentition are taken during scanning, using an intraoral camera. In a design stage of the workflow, a manual administration process is carried out wherein tooth numbers for one or more restorations are input and the position of one or more preparation sites are specified on the 3D model. In the design stage, the scan is also analyzed to generated restoration proposals.

Following the design stage, a manufacturing stage commences wherein the generated restoration proposals are produced by subtractive or additive manufacturing. For example, milling or grinding units are used to produce a physical copy of the restorations. Lastly the restorations can be sintered and glazed to give the restorations their final material and esthetic properties such as hardness, strength, temperature conductivity.

SUMMARY

The illustrative embodiments provide a method, system, and computer program product. One relates to a method that includes forming, using a spline forming module, a spline along a jaw. The method further includes proposing potential interdental gaps, using an interdental gaps proposal module, by performing one or more of the interdental gap detection steps of: analyzing tooth cross-sections using a cross-sections module, detecting interdental papilla using an interdental papilla detection module, and classifying tooth intervals using a classification module. The potential interdental gaps are then weighted based on one or more of the interdental gap detection steps, to obtain one or more delimiters. Further, tooth number probabilities are automatically proposed, for each of one or more possible tooth alignments between at least one pair of fixed delimiters, using an alignments module; and a best fit tooth number distribution is determined from the one or more possible tooth alignments, responsive to the automatically proposing step, using at least the proposed tooth number probabilities. The alignments module is a machine learning engine.

In some implementations, a patient-specific restoration is generated based on the computed best fit tooth number distribution.

In some implementations the interdental gap detection steps are all performed and are performed in parallel.

Another aspect relates to computing the best fit tooth number distribution, using a global optimization module that accelerates the computing of the best fit tooth number distribution, by dynamic programming. The global optimization module uses as input, one or more factors selected from the list consisting of a correspondence between an upper and a lower jaw, sizes of teeth, weights from the weighting step, and an output of the machine learning engine. The best fit tooth number distribution may also be computed using an iteration module, by iterating through all possible tooth alignments about the at least one pair of fixed delimiters.

In some implementations the best fit tooth number distribution is computed for a full dental cavity that includes an upper jaw and a lower jaw. A plurality of delimiters is obtained and a plurality of possible tooth alignments between said at least one pair of fixed delimiters are determined for both the upper jaw and the lower jaw. Tooth number probabilities may be automatically proposed for the plurality of possible tooth alignments, from which the best fit tooth number distribution for the full dental cavity is computed. The best fit tooth number distribution includes both a best fit upper jaw tooth number distribution and a best fit lower jaw tooth number distribution.

In some implementations, in the computation step, the best fit tooth number distribution is computed for one jaw, and another best fit tooth number distribution is inferred for an opposing jaw based on the computed best fit tooth number distribution.

In some implementations, in the computation step, the best fit tooth number distribution is computed for a portion of one jaw, e.g. at least 3-4 teeth. Another best fit tooth number distribution may be inferred for an opposing portion of the jaw or for an opposing portion of an opposing jaw based on the computed best fit tooth number distribution. The portion of one jaw may include eight possible teeth of a first quadrant of the jaw.

In some implementations the forming step is automatic.

In some implementations, the one or more delimiters are potential and/or fixed delimiters based on their respective weights.

In some implementations, at least one tooth preparation type probability between said at least one pair of fixed delimiters are proposed.

In some implementations, at least one of the one or more delimiters indicates a space that is representative of one or more missing teeth.

In some implementations, a space between two delimiters that are beyond a threshold distance apart, is representative of one or more possible teeth. In some implementations, a space between two adjacent delimiters that are below a threshold distance apart, is representative of an interdental gap.

In some implementations, the automatically proposing step predicts a tooth number of said one or more possible teeth that fit inside said space.

In some implementations, at least one of the one or more delimiters indicates a boundary between adjacent teeth.

In some implementations the tooth number probabilities are percentages or values between 0 and 1.

In some implementations, the tooth number probabilities are likelihood evaluations or classifications.

In some implementations, the machine learning engine has a model that is based on a 3D surface based neural network such as Convolutional Neural Network (CNN), a Point Convolutional Neural Network (PointCNN), a PointNet, a PointNet++ etc. CNN works on Images (or 2.5D arrays) whereas PointNet works on the 3D surface.

In another aspect, for each of the one or more possible tooth alignments a preprocessing step is performed by constructing an estimated model representative of a current possible tooth alignment. The constructed estimated model is provided as input to the machine learning model and the tooth number are obtained as output. The estimated model is represented as a 2D array of height values (2.5D image) that correspond to heights (relative to a plane parallel to the occlusal plane) of a plurality surface points of a model. The constructed estimated model may alternatively be a 3D model. The machine learning model may be trained using a training dataset that includes input training models and corresponding output training tooth number. A space in an input training model may be interpreted as corresponding to one or more missing teeth that correspond respectively to one or more same or distinct tooth numbers.

In another aspect, a computing system is disclosed. The computing system includes a processor and a memory that stores instructions that, when executed by the processor, configure the system to form, using a spline forming module, a spline along a jaw. Potential interdental gaps are also proposed, using an interdental gaps proposal module, by performing one or more of the interdental gap detection steps of: analyzing tooth cross-sections using a cross-sections module, detecting interdental papilla using an interdental papilla detection module, and classifying tooth intervals using a classification module. The system weights the potential interdental gaps, based on one or more of the interdental gap detection steps, to obtain one or more delimiters. The system automatically proposes tooth number probabilities, for each of one or more possible tooth alignments between at least one pair of fixed delimiters using an alignments module and the system computes a best fit tooth number distribution, from the one or more possible tooth alignments, responsive to the automatically proposing step, using at least the proposed tooth number probabilities. The alignments module is a machine learning engine. A patient-specific restoration may be generated based on the computed best fit tooth number distribution. The machine learning engine has a model that is based on a Convolutional Neural Network (CNN) or a Point Convolutional Neural Network (PointCNN).

In yet another aspect, a non-transitory computer-readable storage medium is disclosed. The non-transitory computer-readable storage medium includes instructions that when executed by a computer, cause the computer to form, using a spline forming module, a spline along a jaw; propose potential interdental gaps, using an interdental gaps proposal module, by performing one or more of the interdental gap detection steps of: analyzing tooth cross-sections using a cross-sections module, detecting interdental papilla using an interdental papilla detection module, and classifying tooth intervals using a classification module; weight the potential interdental gaps, based on one or more of the interdental gap detection steps, to obtain one or more delimiters; automatically propose tooth number probabilities, for each of one or more possible tooth alignments between at least one pair of fixed delimiters, using an alignments module; and compute a best fit tooth number distribution, from the one or more possible tooth alignments, using at least the proposed tooth number probabilities. The alignments module is a machine learning engine.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

BRIEF DESCRIPTION OF THE DRAWINGS

Certain novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

DETAILED DESCRIPTION

Figure 1:
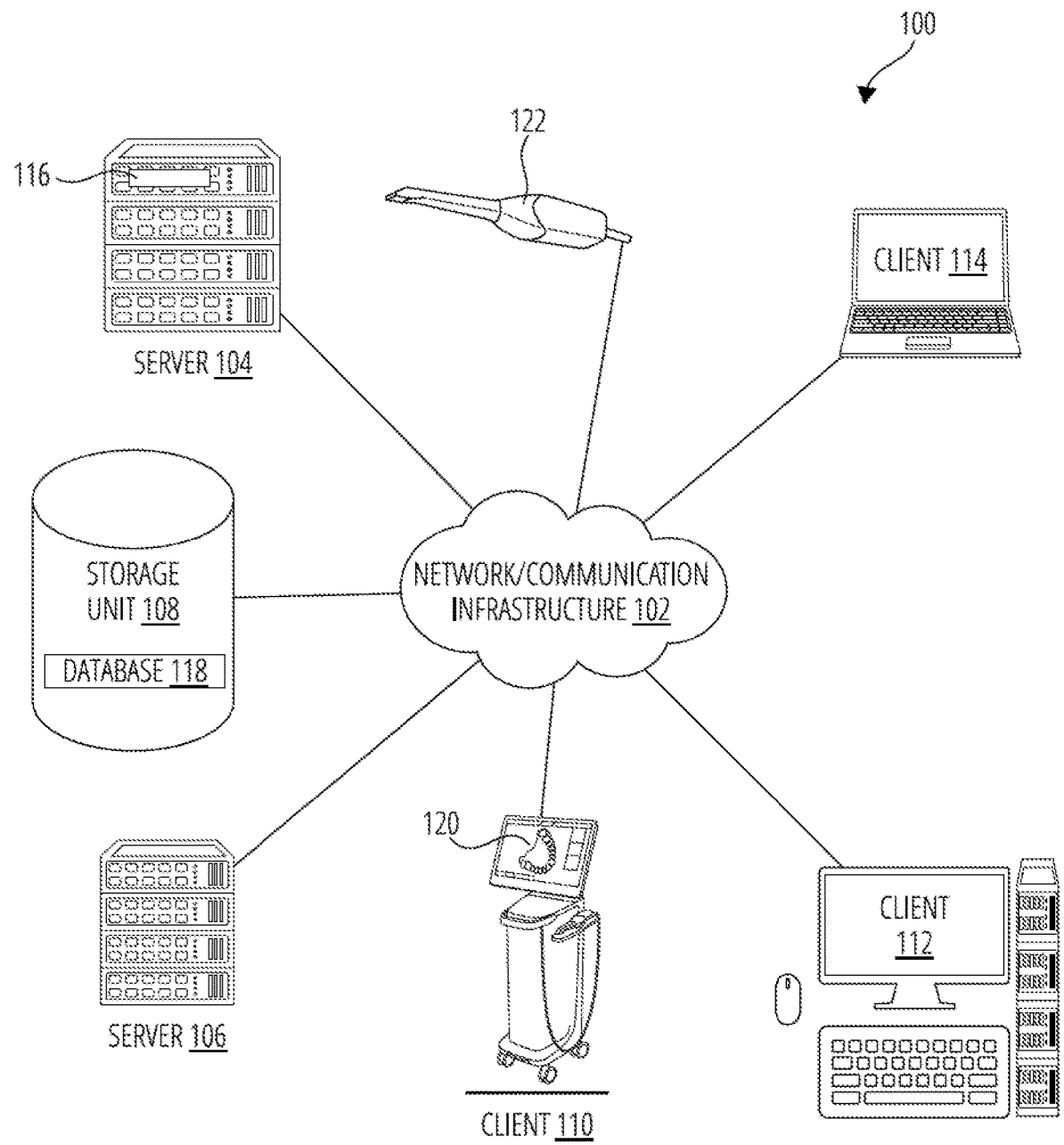
FIG. 1 depicts a block diagram of a network of data processing systems in which illustrative embodiments may be implemented.

The illustrative embodiments recognize that the user of any Computer-aided design (CAD) software for restoration creation unnecessarily deals with the manual placement of restorations or choosing of restoration types at two instances in a restoration workflow, once at the beginning of a design stage in the workflow by the definition of tooth number and tooth indication using on a tooth diagram or tooth scheme (e.g. two-dimensional (2D) tooth diagram), and then after a three-dimensional (3D) model creation by the use of the scanned areas of the 3D jaw through the entering or choosing of the position of the restoration (which is typically done by defining the preparation margin). The illustrative embodiments recognize that this is not only time-consuming but also error-prone, especially for new dental professionals. The illustrative embodiments recognize that this is a particularly challenging problem to solve, one that is not known to be solved in currently available solutions. The illustrative embodiments recognize that in conventional software, the tooth numbers of prepared teeth as well as the position of prepared sites the 3D model must be specified. Further, corrections to these inputs by the user must also be made in the same way. This demands significant user interaction and thus more opportunities to generate errors. A need exists for automating this and other stages of the restoration process to deliver and enhance the accuracy of proposed restorations. A need exists for a fully automatic recognition and calculation that enables restoration designs without user interaction after the jaws have been scanned or after jaw models have been imported such that prepared areas on tooth models can be automatically recognized and classified to aid in the generation of tooth proposals. A need further exists for user-friendly tools to provide users with correction tools for intuitive adjustment of the cavity and correcting incorrect restoration positioning directly on the 3D model using simple drag and drop actions. The illustrative embodiments used to describe the invention generally address and solve the above-described problems and other related problems by automating the tooth administration phase such as all tooth manual management process of a restoration workflow and thus automating the entire or substantial portion of the restoration workflow, excluding for example, the tooth scanning process.

An embodiment automatically generates restorations without prior manual input of restoration indications, tooth numbers or tooth positions on a model. The embodiment displays the generated restorations on the 3D model. The embodiment presents a tool for fine adjustment of cavity regions that are not completely accurate. The embodiment presents a tool for adjustment of restoration position if needed.

The illustrative embodiments are described with respect to certain types of data, functions, algorithms, equations, model configurations, locations of embodiments, additional data, devices, data processing systems, environments, components, and applications only as examples. Any specific manifestations of these and other similar artifacts are not intended to be limiting to the invention. Any suitable manifestation of these and other similar artifacts can be selected within the scope of the illustrative embodiments.

Furthermore, the illustrative embodiments may be implemented with respect to any type of data, data source, or access to a data source over a data network. Any type of data storage device may provide the data to an embodiment of the invention, either locally at a data processing system or over a data network, within the scope of the invention. Where an embodiment is described using a mobile device, any type of data storage device suitable for use with the mobile device may provide the data to such embodiment, either locally at the mobile device or over a data network, within the scope of the illustrative embodiments.

The illustrative embodiments are described using specific code, designs, architectures, protocols, layouts, schematics, and tools only as examples and are not limiting to the illustrative embodiments. Furthermore, the illustrative embodiments are described in some instances using particular software, tools, and data processing environments only as an example for the clarity of the description. The illustrative embodiments may be used in conjunction with other comparable or similarly purposed structures, systems, applications, or architectures. For example, other comparable devices, structures, systems, applications, or architectures therefor, may be used in conjunction with such embodiment of the invention within the scope of the invention. An illustrative embodiment may be implemented in hardware, software, or a combination thereof.

The examples in this disclosure are used only for the clarity of the description and are not limiting to the illustrative embodiments. Additional data, operations, actions, tasks, activities, and manipulations will be conceivable from this disclosure and the same are contemplated within the scope of the illustrative embodiments.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Figure 2:
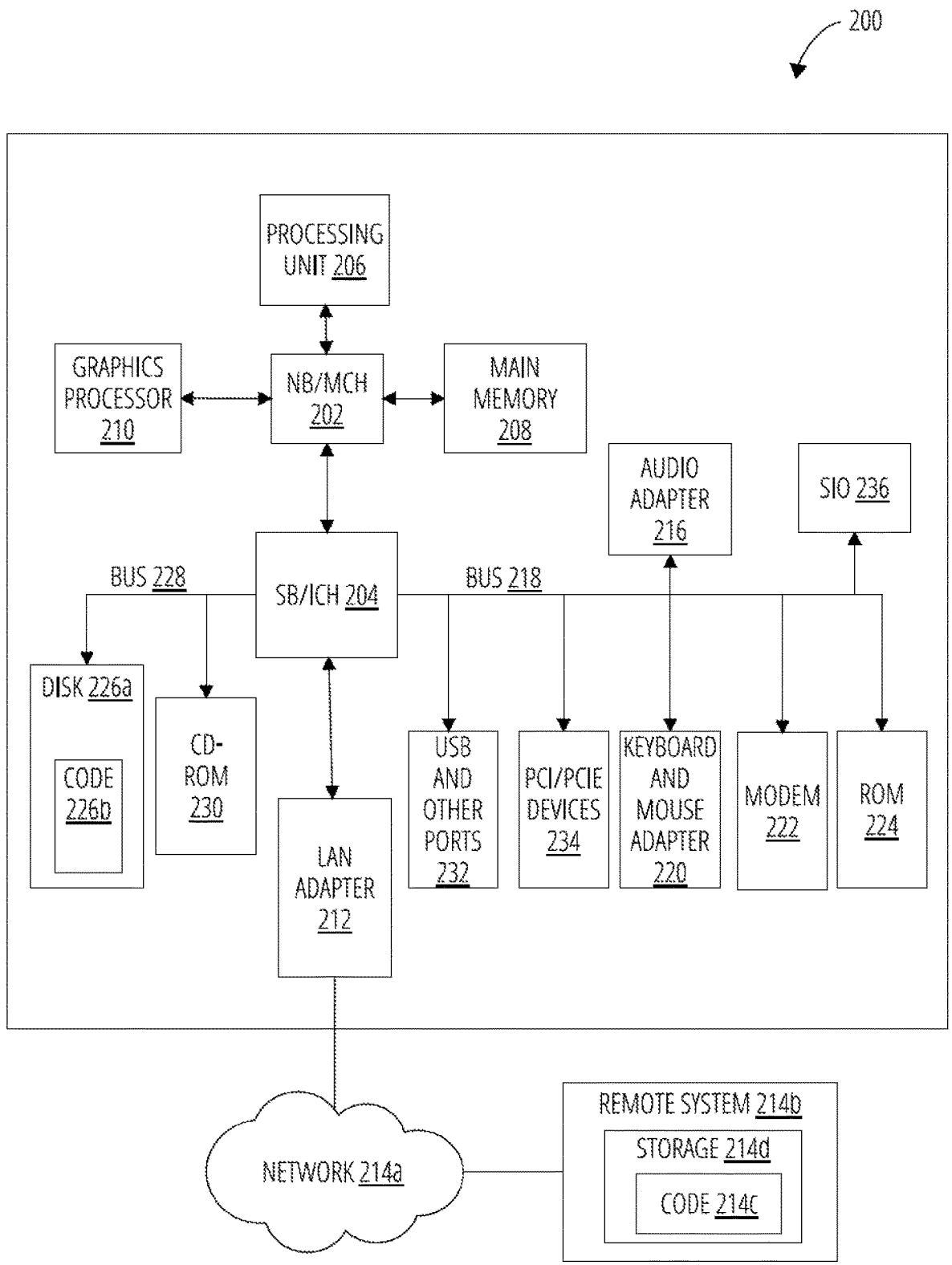
FIG. 2 depicts a block diagram of a data processing system in which illustrative embodiments may be implemented.

With reference to the figures and in particular with reference to FIG. 1 and FIG. 2, these figures are example diagrams of data processing environments in which illustrative embodiments may be implemented. FIG. 1 and FIG. 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment 100 is a network of computers in which the illustrative embodiments may be implemented. Data processing environment 100 includes network/communication infrastructure 102. Network/communication infrastructure 102 is the medium used to provide communications links between various devices, databases and computers connected together within data processing environment 100. Network/communication infrastructure 102 may include connections, such as wire, wireless communication links, or fiber optic cables.

Clients or servers are only example roles of certain data processing systems connected to network/communication infrastructure 102 and are not intended to exclude other configurations or roles for these data processing systems. Server 104 and server 106 couple to network/communication infrastructure 102 along with storage unit 108. Software applications may execute on any computer in data processing environment 100. Client 110, client 112, client 114 are also coupled to network/communication infrastructure 102. Client 110 may be a dental acquisition unit with a display. A data processing system, such as server 104 or server 106, or clients (client 110, client 112, client 114) may contain data and may have software applications or software tools executing thereon.

Only as an example, and without implying any limitation to such architecture, FIG. 1 depicts certain components that are usable in an example implementation of an embodiment. For example, servers and clients are only examples and do not to imply a limitation to a client-server architecture. As another example, an embodiment can be distributed across several data processing systems and a data network as shown, whereas another embodiment can be implemented on a single data processing system within the scope of the illustrative embodiments. Data processing systems (server 104, server 106, client 110, client 112, client 114) also represent example nodes in a cluster, partitions, and other configurations suitable for implementing an embodiment.

Dental scanner 122 includes one or more sensors that measure teeth by obtaining a plurality of images through projections that map a person's oral cavity. In an example, the dental scanner 122 captures data points as often as several hundred or thousand times each second, automatically registering the sizes and shapes of each tooth. It continuously sends this data to the connected computer's software, which builds it into a 3D impression of the patient's oral cavity.

A most widely used digital format is the STL (Standard Tessellation Language) format but other formats can also be used. This format describes a succession of triangulated surfaces where each triangle is defined by three points and a normal surface. STL files may describe only the surface geometry of a three-dimensional object without any representation of color, texture or other CAD model attributes. However, other file formats have been developed to record color, transparency, or texture of dental tissues (such as Polygon File Format, PLY files). Irrespective of the type of imaging technology employed, scanners or cameras project light that is then recorded as individual images and compiled by the software after recognition of POI (points of interest). For example, two coordinates (x and y) of each point are evaluated on the image, and the third coordinate (z) is then calculated depending on a distance from the scanner.

Client application 120 or any other application 116 implements an embodiment described herein. Client application 120 can use data from dental scanner 122 to generate or render 3D models using single frame images taken by the dental scanner 122. Client application 120 can also obtain data from storage unit 108 for rendering or characterization. Client application 120 can also execute in any of data processing systems (server 104 or server 106, client 110, client 112, client 114), such as client application 116 in server 104 and need not execute in the same system as client 110.

Server 104, server 106, storage unit 108, client 110, client 112, client 114, may couple to network/communication infrastructure 102 using wired connections, wireless communication protocols, or other suitable data connectivity. Client 110, client 112 and client 114 may be, for example, personal computers or network computers.

In the depicted example, server 104 may provide data, such as boot files, operating system images, and applications to client 110, client 112, and client 114. Client 110, client 112 and client 114 may be clients to server 104 in this example. Client 110, client 112 and client 114 or some combination thereof, may include their own data, boot files, operating system images, and applications. Data processing environment 100 may include additional servers, clients, and other devices that are not shown. Server 104 includes an application 116 that may be configured to implement one or more of the functions described herein for displaying a live control view in accordance with one or more embodiments.

Server 106 may include a search engine configured to search or retrieve stored files such as images and 3D models of patients for a dental practice in response to a request from an operator as described herein with respect to various embodiments.

In the depicted example, data processing environment 100 may be the internet. Network/communication infrastructure 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such client 110, client 112, client 114 or s server 104, server 106, in FIG. 1, or another type of device in which computer usable program code or instructions implementing the processes may be located for the illustrative embodiments.

Data processing system 200 is described as a computer only as an example, without being limited thereto. Implementations in the form of other devices, in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to North Bridge and memory controller hub (NB/MCH) 202 through an accelerated graphics port (AGP) in certain implementations.

In the depicted example, local area network (LAN) adapter 212 is coupled to South Bridge and input/output (I/O) controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and input/output (I/O) controller hub (SB/ICH) 204 through bus 218. Hard disk drive (HDD) or solid-state drive (SSD) 226a and CD-ROM 230 are coupled to South Bridge and input/output (I/O) controller hub (SB/ICH) 204 through bus 228. PCI/PCIe devices 234 may include, for example, Ethernet adapters, add-in cards, and PC cards for notebook computers. PCI uses a card bus controller, while PCIe does not. Read only memory (ROM) 224 may be, for example, a flash binary input/output system (BIOS). Hard disk drive (HDD) or solid-state drive (SSD) 226a and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and input/output (I/O) controller hub (SB/ICH) 204 through bus 218.

Memories, such as main memory 208, read only memory (ROM) 224, or flash memory (not shown), are some examples of computer usable storage devices. Hard disk drive (HDD) or solid-state drive (SSD) 226a, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object oriented or other type of programming system may operate in conjunction with the operating system and provide calls to the operating system from programs or applications executing on data processing system 200.

Instructions for the operating system, the object-oriented programming system, and applications or programs, such as application 116 and client application 120 in FIG. 1, are located on storage devices, such as in the form of codes 226b on Hard disk drive (HDD) or solid-state drive (SSD) 226a, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory (ROM) 224, or in one or more peripheral devices.

Furthermore, in one case, code 226b may be downloaded over network 214a from remote system 214b, where similar code 214c is stored on a storage device 214d in another case, code 226b may be downloaded over network 214a to remote system 214b, where downloaded code 214c is stored on a storage device 214d.

The hardware in FIG. 1 and FIG. 2 may vary depending on the implementation. Other internal hardware or peripheral devices, such as flash memory, equivalent non-volatile memory, or optical disk drives and the like, may be used in addition to or in place of the hardware depicted in FIG. 1 and FIG. 2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I/O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub (NB/MCH) 202. A processing unit may include one or more processors or CPUs.

The depicted examples in FIG. 1 and FIG. 2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and Hard disk drive (HDD) or solid-state drive (SSD) 226a is manifested as a virtualized instance of all or some portion of Hard disk drive (HDD) or solid-state drive (SSD) 226a that may be available in the host data processing system. The host data processing system in such cases is represented by data processing system 200.

Figure 3:
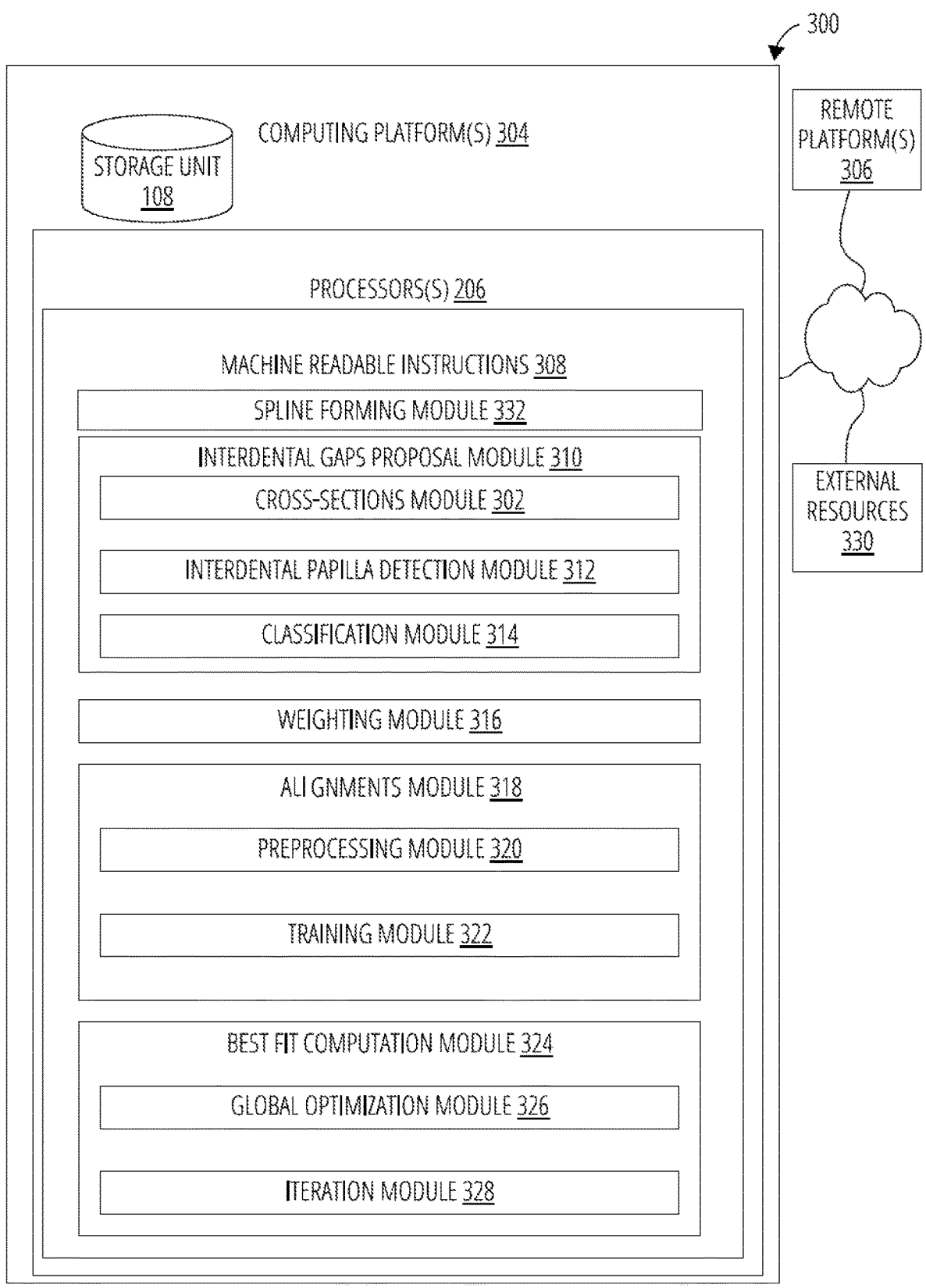
FIG. 3 depicts a block diagram of a restoration system for automated tooth administration in accordance with an illustrative embodiment.

FIG. 3 illustrates a restoration system 300 configured for automating a restoration process, in accordance with illustrative embodiments. In some embodiments, restoration system 300 may include one or more computing platform(s) 304. Computing platform(s) 304 may be configured to communicate with one or more remote platform(s) 306 according to a client/server architecture, a peer-to-peer architecture, and/or other architectures. Remote platform(s) 306 may be configured to communicate with other remote platforms via computing platform(s) 304 and/or according to a client/server architecture, a peer-to-peer architecture, and/or other architectures. Users may access restoration system 300 via remote platform(s) 104.

Computing platform(s) 304 may be configured by machine-readable instructions 308. Machine-readable instructions 308 may include one or more instruction modules. The instruction modules may include one or more of a spline forming module 332, an interdental gaps proposal module 310, a cross-sections module 302, an interdental papilla detection module 312, a classification module 314, a weighting module 316, an alignments module 318, a pre-processing module 320, a training module 322, a best fit computation module 324, a global optimization module 326, an iteration module 328, and/or other instruction modules. Remote platform(s) 306 and external resources 330 may correspond to the servers and client applications of the data processing environment 100. In an illustrative embodiment, the computing platform(s) 304 may execute the methods or processes described herein such as the processes of FIG. 4, FIG. 15, FIG. 16, FIG. 19, FIG. 12 and FIG. 17. The processes may be executed such that compared to a conventional workflow, restorations do not have not to be defined explicitly, tooth numbers do not have to be indicated, preparation types do not have to be indicated, restorations are proposed directly in a 3D scene on a display without user interaction, the jaw model does not have to be manually positioned, insertion axes do not have to be manually input, no initial input of preparation margins are needed, scan bodies (abutments) do not have to be marked, construction axes (abutments) do not have to be input, if necessary, intuitive adjustment of the cavity with restoration already in place can be done, and if necessary, wrong tooth positioning can be corrected by drag & drop in the 3D scene.

Figure 4:
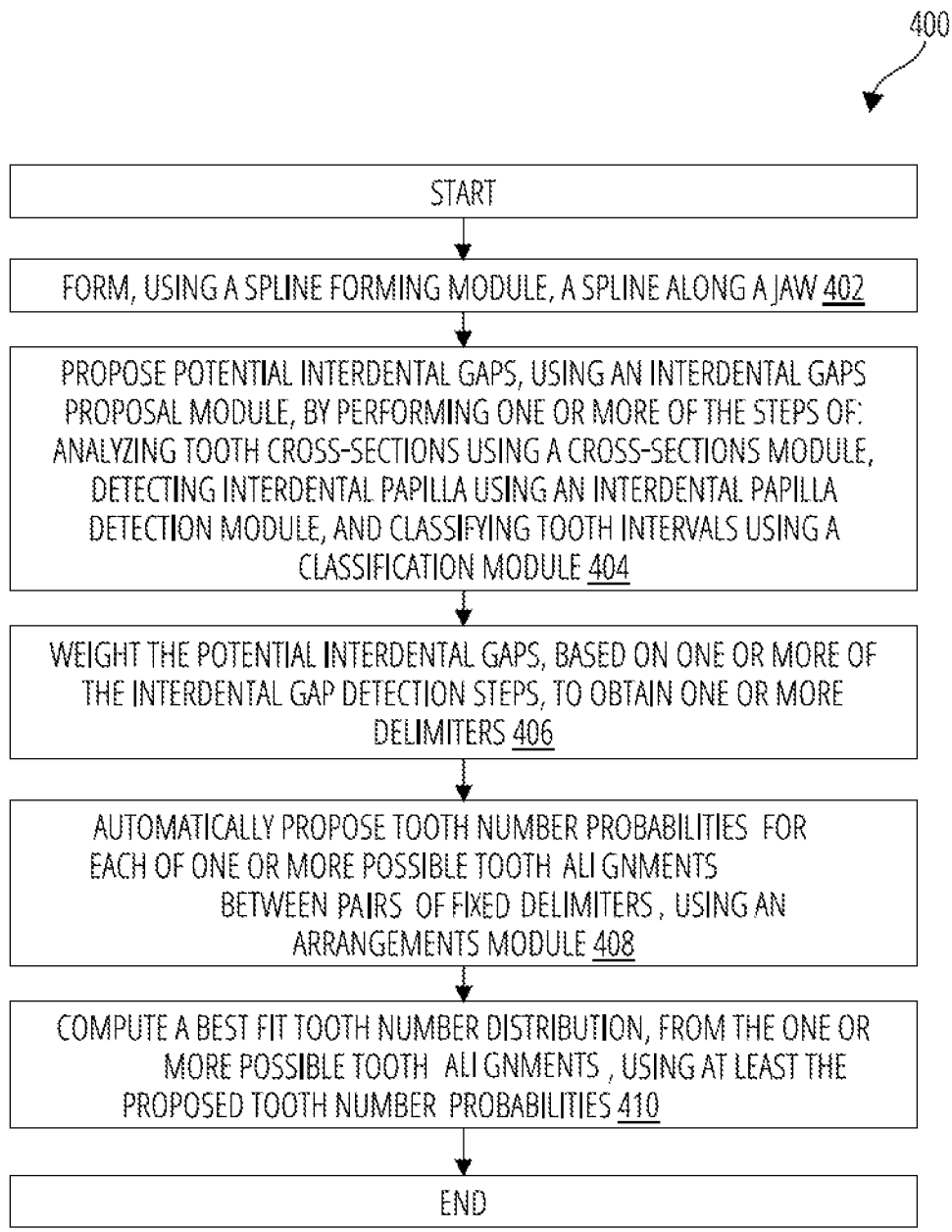
FIG. 4 depicts a method for automated tooth administration, in accordance with one or more illustrative embodiments.

Turning now to FIG. 4, a process 400 performed by the computing platform(s) 304 of FIG. 3 will be described. The process begins at step 402. In step 402, process 400 forms, using the spline forming module 332, a spline along a jaw. In step 404, process 400 proposes potential interdental gaps, using an interdental gaps proposal module, by performing in one or more of the interdental gap detection steps of: (a) analyzing tooth cross-sections using the cross-sections module 302, (b) detecting interdental papilla using the interdental papilla detection module 312, and (c) classifying tooth intervals using the classification module 314. In an illustrative embodiment, all three steps are performed together in parallel. In another embodiment, any combination of the steps is performed serially or in parallel. In step 406, process 400 weights the potential interdental gaps using the weighting module 316, the weighting being done based on one or more of the interdental gap detection steps, to obtain one or more delimiters. In an illustrative embodiment, a user may scan at least three but if a scan is a lot shorter than required and contains only the transition of two tooths, then only one delimiter may be obtained. Further, it may be sufficient to scan at least three teeth on one jaw. In particular, drilling templates are mostly constructed only on the lower or upper jaw and therefore only one side of the jaw may be scanned.

In step 408, process 400 automatically proposes tooth number probabilities for each of one or more possible tooth alignments between fixed delimiters (e.g. adjacent fixed delimiters), using the alignments module 318 as explained hereinafter. In an embodiment, the alignments module 318 is a machine learning engine. In step 410, process 400 computes a best fit tooth number distribution, using a best fit computation module 324, from the one or more possible tooth alignments, using at least the proposed tooth number probabilities.

Figure 5:
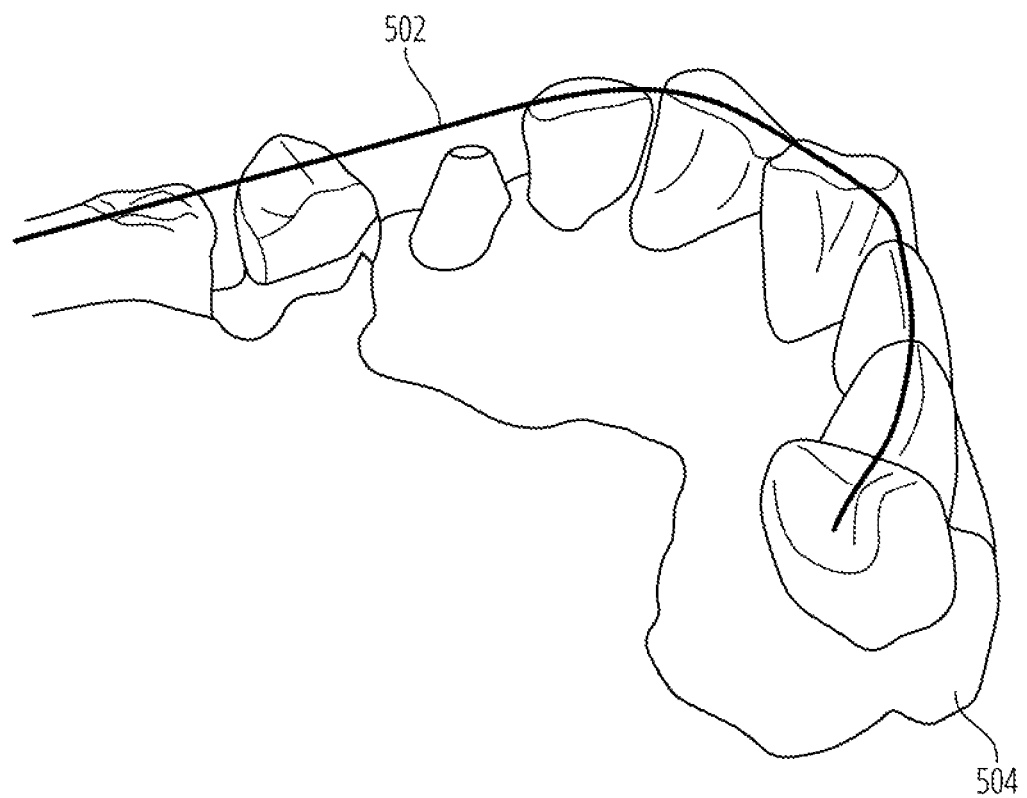
FIG. 5 depicts a 3D model in accordance with one or more illustrative embodiments.

In step 402, a spline curve 502, as shown in FIG. 5 is fitted along the upper and the lower jaw of a 3D model 504 obtained from the scanning of a patient's dentition. The fitting leads to a smooth line which can be used as reference line for all further calculations. The fitting process may begin with a crude line that is fitted on surfaces of the teeth. Parts of the crude line are divided into two points and repositioned onto the jaw in a refinement process. This is done by statistical calculations that include weighting points on the jaw based on how important (e.g. nearer to the fissure/incisal edge) they are for teeth. Usually the higher the point, the most relevant they are. For the statistics all vertices of the triangulation are used, where those lying nearer to the fissure/incisal edge have the higher weights Alternatively, a solution where an analytical spline is directly fit on the jaw by optimizing some control vertices of the spline is possible. In this case no refinement is needed. The spline curve 502 may be fitted on top fissures in the molar teeth and on surfaces of the incisors such as the incisal edges. Further, a combined/averaged spline of the lower and upper jaw spline is created as a generalized parametrization curve for the entire dentition. The spline curve 502 is used as a reference line for one or more calculations described herein.

In step 404 potential interdental gaps (spaces between teeth) are proposed using a number of interdental gap detection procedures. In an illustrative embodiment, three procedures are carried out in parallel, though they may also be serially carried out. This includes (a) analyzing tooth cross-sections using the cross-sections module 302, (b) detecting interdental papilla using the interdental papilla detection module 312, and (c) classifying tooth intervals using the classification module 314.

Figure 6:
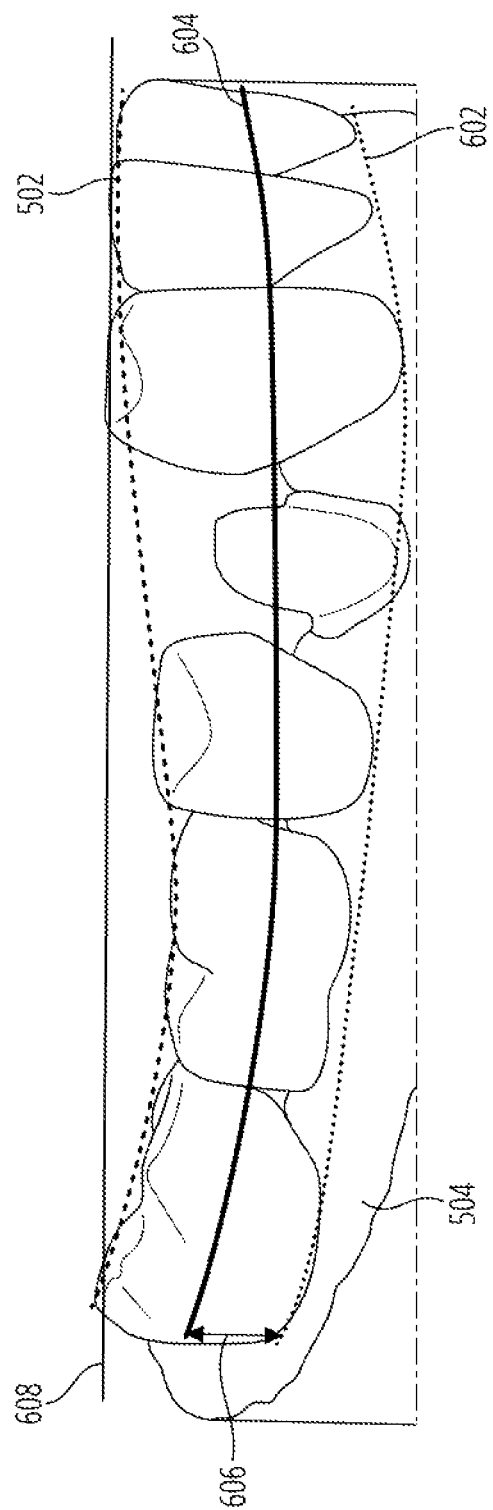
FIG. 6 depicts a 3D model in accordance with one or more illustrative embodiments.

The step of finding potential interdental gaps by analyzing tooth cross-sections can be carried out in an illustrative embodiment as follows. A height 606 to be used for the cross-section is found for every position along the cross-section as shown in FIG. 6. Given the spline curve 502, and a transition curve 602 representative of a transition between the teeth and gingiva (the spline curve 502 and transition curve 602 ideally contain the same number of points), a cross-sectional curve 604 is obtained by finding a height, for each point pair on the spline curve 502 and transition curve 602, that is a defined ratio between the point pairs. In an example, the position on the cross-sectional curve 604 is one-third of the distance between a corresponding position on the transition curve 602 and a corresponding position on the spline curve 502. In another example, the spline curve 502 is lowered into the middle of the jaw or moved, e.g. a defined distance along a plane perpendicular to the occlusal plane such that the cross-sectional curve 604 appears superimposed on the spline curve 502 when viewed from above/from the perspective of the occlusal plane 608. Of course, the examples given are not meant to be limiting and other reference lines/curves and ratios that provide a consistent frame of reference for the processes described herein can be obtained in light of the descriptions.

The cross-sectional curve 604 remains at the same level (the cross section is kept in a fixed ratio between spline curve 502 and transition curve 602) over preparations so that preparations can be correctly distinguished from healthy teeth. More specifically, the cross-sectional curve 604 should work for marginal preparations, i.e. the analysis with help of the cross-section can recognize all types of preparations like inlays, onlays, partial crowns etc.

Figure 7A:
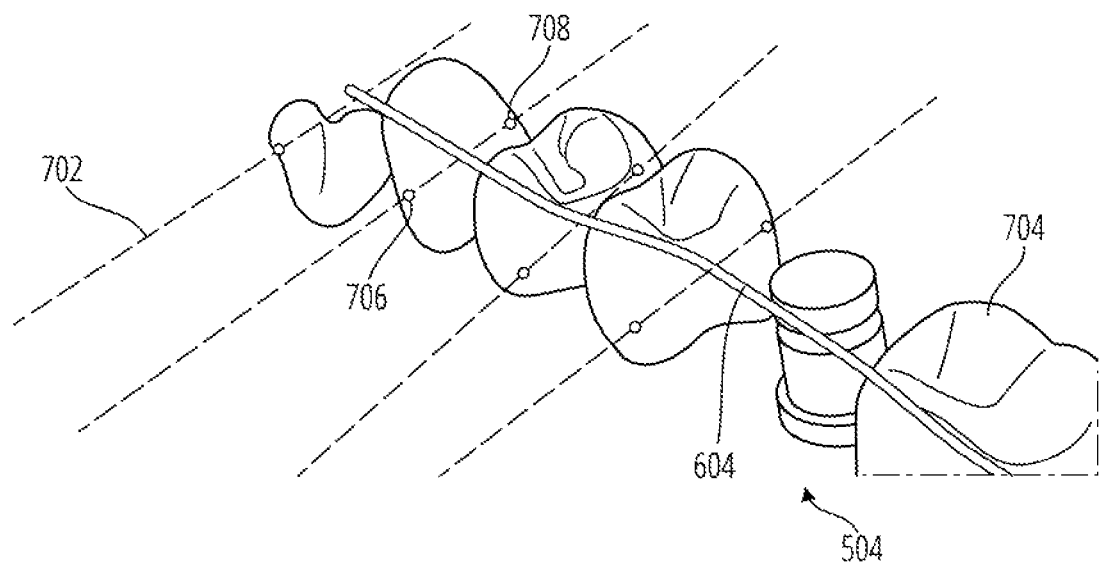
FIG. 7A depicts a 3D model in accordance with one or more illustrative embodiments.
Figure 7B:
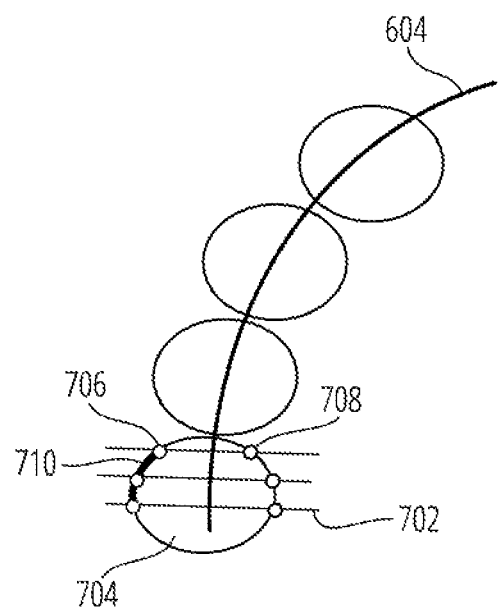
FIG. 7B depicts a 2D representation of a jaw in accordance with one or more illustrative embodiments.

Subsequently, a bilateral distance function is computed. The computation is shown in FIG. 7A-FIG. 7B wherein the cross-sectional curve 604 is sampled with a defined length resolution of, for example, approximately 100 samples per tooth 704 (such as 80-120 samples). A perpendicular line 702 that is perpendicular to the cross-sectional curve 604 is placed through each sample at the height of the cross-sectional curve 604. The directions of these lines also lie in the occlusal plane 608. The perpendicular lines 702 intersect with the 3D model 504 and a lingual intersection point 706 and a buccal/labial intersection point 708 are determined in each case, with potential inter-section points lying on an opposite side of the mandibular arch being excluded in an illustrative embodiment. FIG. 7B shows an 2D (two dimensional) view of the bilateral distance function computation according to an illustrative embodiment wherein a plurality of perpendicular lines 702 are shown as passing through one tooth 704.

By determining the plurality of lingual intersection points 706 and buccal/labial intersection points 708 for all teeth being examined, and connecting them to form a contour line 710, the minima 804 (local minimum of the distances between points on the contour line 710 on one side of the teeth and corresponding points on the cross-sectional curve 604) as well as gaps 802 (areas showing the start or end of contour lines 710) may be obtained. The gaps 802 and minima 804 are candidates for interdental gaps, i.e. representative of potential interdental gaps/boundaries between teeth as shown by FIG. 8A, FIG. 8B and FIG. 8C, which are representative of the first seven teeth of an illustrative jaw with the remaining teeth being truncated.

Figure 8A:
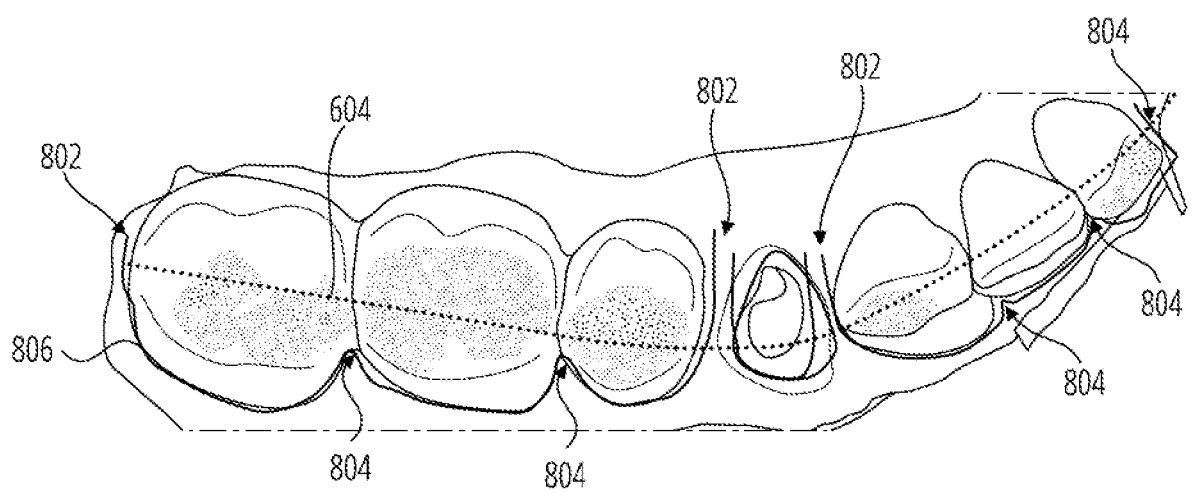
FIG. 8A depicts a 3D model in accordance with one or more illustrative embodiments.
Figure 8B:
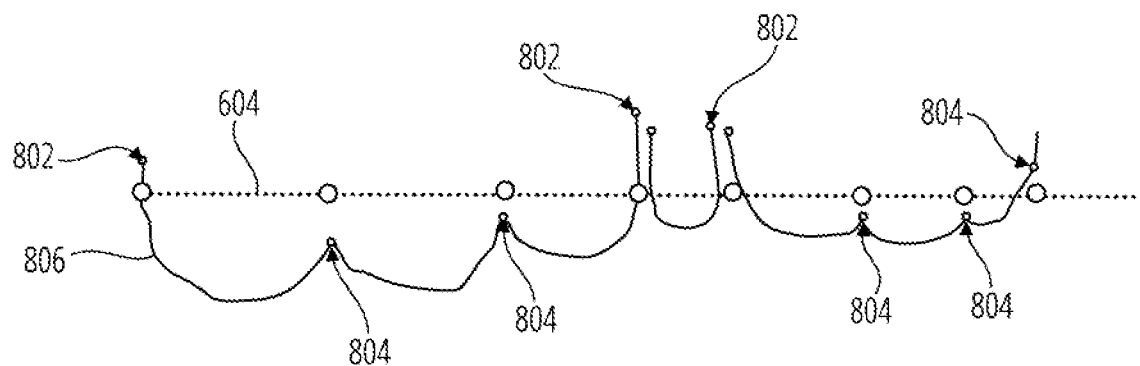
FIG. 8B depicts a 2D representation of a jaw in accordance with one or more illustrative embodiments.
Figure 8C:
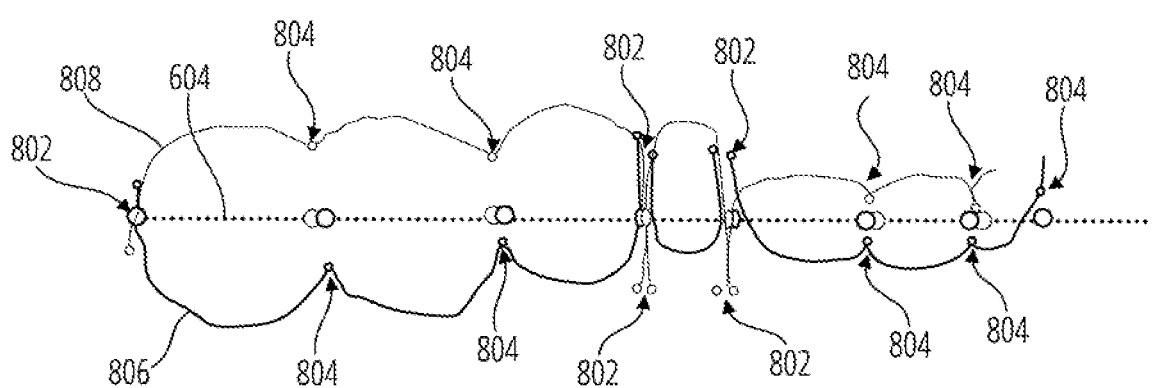
FIG. 8C depicts a 2D representation of a jaw in accordance with one or more illustrative embodiments.

FIG. 8A shows a buccal contour line 806 along with corresponding gaps 802 and minima 804. By straightening the cross-sectional curve 604, as shown in FIG. 8B, a common frame of reference may be obtained to enable the addition of the lingual contour line 808 of FIG. 8C on the other side of the teeth. By finding the gaps 802 and minima 804 for both the buccal contour line 806 and lingual contour line 808, detection of potential interdental gaps is made in a more stable manner compared to performing the process for just one side. This is due to the observation that minima 804 and gaps 802 from either side that are located near each other with respect to the cross-sectional curves 604 are more statistically likely to be representative of actual interdental gaps/actual boundaries between teeth. Thus gaps 802 and minima 804 or features thereof can be weighted in a weighting process by a weighting module 316 as described hereinafter.

Figure 10A:
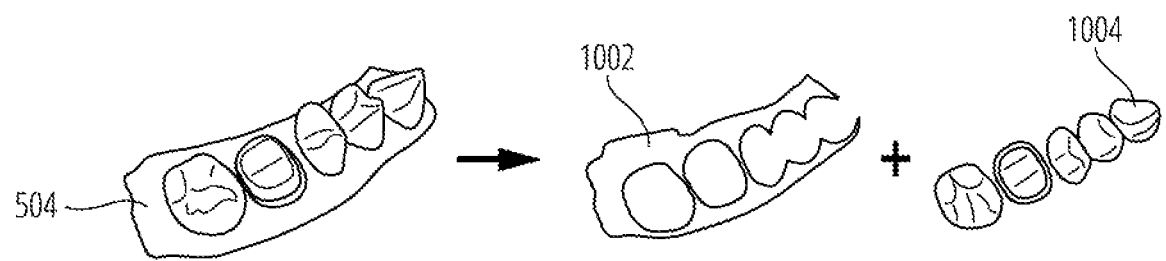
FIG. 10A depicts a segmentation process in accordance with one or more illustrative embodiments.

In another interdental gap detection process, the interdental gaps are obtained by detecting interdental papilla. This may be achieved with the interdental papilla detection module 312. The process includes segmenting the scan of the patient's teeth into segmented gingiva 1002 and segmented teeth 1004 as shown in FIG. 10A. Based on the gingiva segmentation, the interdental papillae can be found. If the gingiva segmentation is correct, proximal areas can also be found in fully prepared teeth. The procedure is carried out in three steps.

In a first step, a spatial curve along the boundary between teeth and gingiva is segmented. Two separate spatial curves along the buccal and the lingual side of the gingiva are then determined.

Figure 10B:
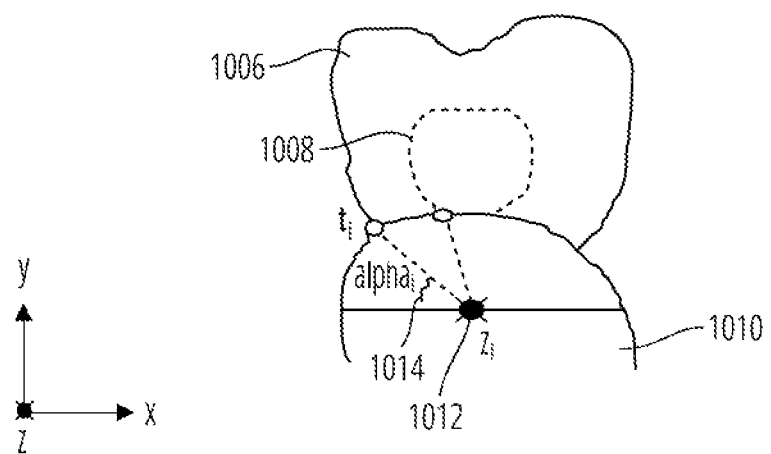
FIG. 10B depicts a cross section of a jaw in accordance with one or more illustrative embodiments.
Figure 11:
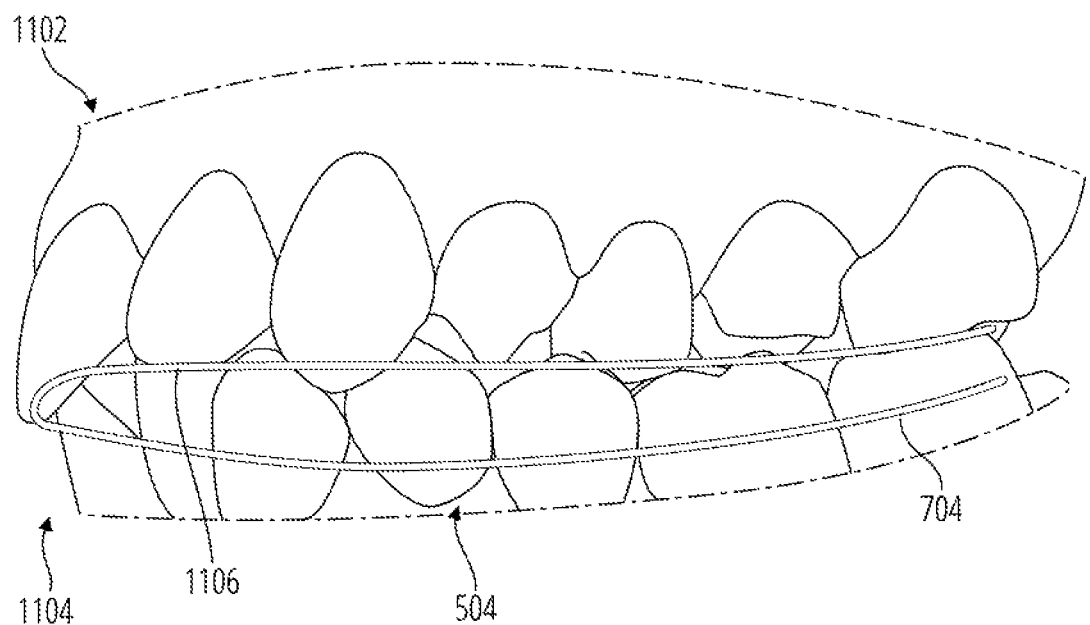
FIG. 11 depicts a 3D model in accordance with one or more illustrative embodiments.
Figure 12:
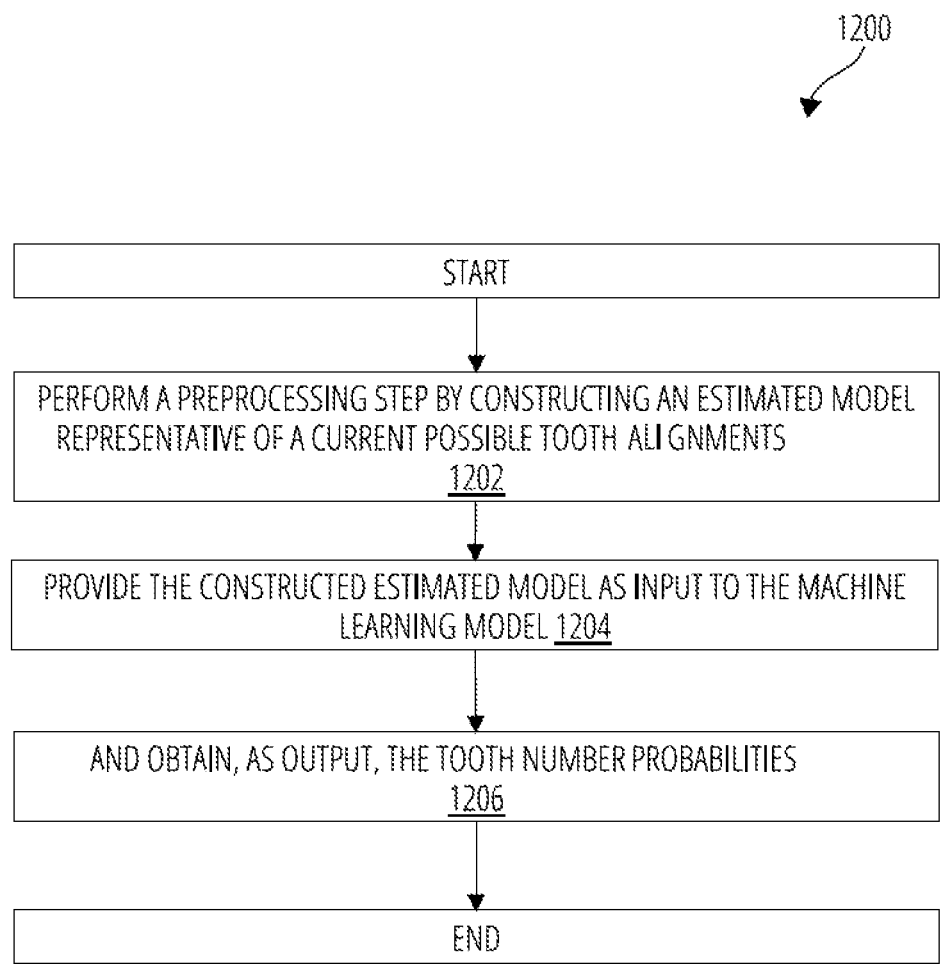
FIG. 12 depicts a process in accordance with one or more illustrative or more illustrative embodiments.

In a second step, an angle function describing the course of the gingival boundary is determined along the jaw ridge line both buccally and lingually. As shown in FIG. 10B, which shows a cross section of the jaw in a crown-to-gingiva direction, to achieve a combined assessment of the heights of the margins in the occlusal direction and the widths in a lingual-buccal direction an angle function along a reference line is defined as seen from positions placed at the center of the jaw 1010. The cross section is perpendicular to a jaw center line/curve 1012 described herein. The jaw center line/curve 1012, extends in the z-direction as shown in FIG. 10B, and corresponds in shape to the spline curve 502 when viewed from above (a crown direction). For every sample position $z_i$ along the jaw center line/curve 1012, the angle alpha-i to the lingual and to the buccal gingiva curves (in the cross-sectional plane xy) is calculated and stored as a lingual and a buccal angle function. Calculating the angles to the curves is possible due to the segmentation process that separate the teeth from the gingiva.

The third step is carried out as follows. For the two gingival boundary functions, the local maxima, representative of a papillae are determined. Specifically, a plurality of alpha-i angles are computed for first tooth or preparation 1006 and another plurality of alpha-i angles are computed for adjacent tooth or preparation 1008. A potential interdental papilla, and thus a potential interdental gap present between the first tooth or preparation 1006 and the adjacent tooth or preparation 1008 will therefore be determined by, or based on, the largest alpha-i angles or areas between adjacent largest alpha-i angles. Thus, the procedure described above has its maxima values at the interdental papilla and gaps where teeth are missing. Therefore, for the maxima and gaps are extracted and weighted, by a weighting module 316 as described hereinafter, based on their shape characteristics, resulting in fixed or potential delimiters.

In yet another interdental gap detection process, interdental gaps can be determined based on classification of tooth intervals/regions by a classification module 314. Using a max-flow-min-cut optimization process, teeth are segmented from a jaw, given samples along spline curve 502. In an embodiment where both the upper jaw 1102 and lower jaw 1104 are analyzed, a modified spline curve 1106 computed from averaging the spline curve 502 of the upper jaw and the spline curve 502 of the lower jaw may be used. The max-flow-min-cut optimization process involves a flow network wherein a maximum amount of flow passing from a source or starting position to a sink or ending position is equal to the smallest total weight of the edges (minimum cut) which if removed would disconnect the source from the sink. For teeth, the max-flow-min-cut optimization begins by finding a starting position on the surface of a tooth. The start (source) may be somewhere at the occlusal side of the tooth, the sink being defined as all vertices that away from this start position at given distance, and thus lay somewhere on the gingiva or a neighboring tooth. The edge weights for the flow are obtained from the curvature of the surface and the strongest color transitions, resulting in a minimum cut along the edges at the tooth neck. In an example, the stalling position on the tooth surface may be found by projecting a line from a first position or point on the modified spline curve 1106 onto the tooth 704. The process deduces that for some millimeters around the starting position on the tooth there will be tissue/gingiva. The edges of the tooth surface are thus evaluated wherein sharp edges/high curvatures (areas with large gradient changes or large changes in surface normal directions between adjacent points, representative of a transition between gingiva and tooth surfaces) are identified. In a global optimization process, a line along the sharp edges is computed. Having computed the line, which represents a boundary between tooth surfaces and the gingiva on the cervical side, and a separation between neighboring teeth on the distal and mesial sides, the regions within the line are identified (such as colored) to show a distinct tooth. This may be repeated for several starting positions based on corresponding projections from the modified spline curve 1106.

For every region, all points are projected onto the modified spline curve but only the local maxima points of a region with respect to the spline are stored. These maxima are representative of potential and/or fixed delimiters on a common reference line. In an example, all vertices of the segmented tooth are projected to the reference line. The maximal expansion of these projections on the reference line are detected and for that the projection with the minimal and maximal parameter value on the reference line is selected. These positions correspond to the start and the end of the tooth. Further, some of the identified tooth regions end correctly at the gingiva border/boundary while others do not. By discretizing the tooth region borders and performing regression analysis, the potential and/or fixed delimiters can be derived.

Though any combination, such as all of the interdental gap detection steps may be performed in parallel, it is envisioned that any combination of the steps may be performed serially. For example, in an embodiment where a real-time or fast automation of the administration phase of a restoration workflow and subsequent generation of a restoration proposal is not needed, any combinations of said steps may be performed one after the other.

Figure 9A:
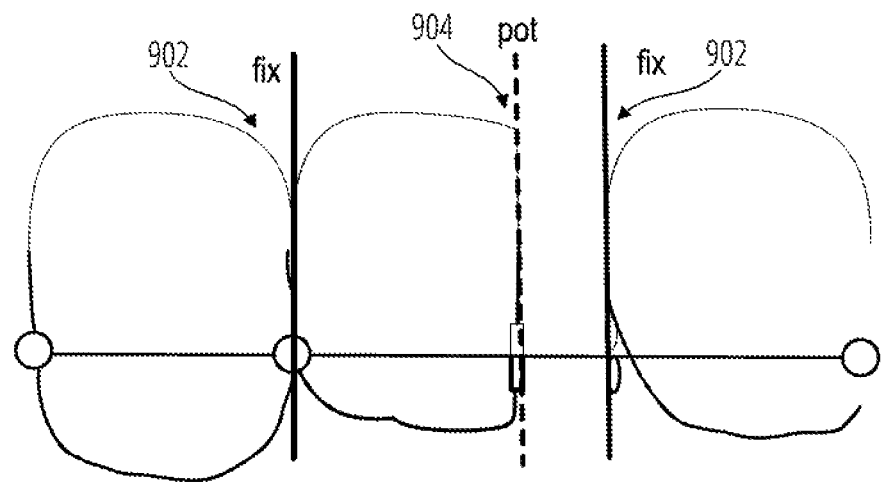
FIG. 9A depicts a 2D representation of a jaw in accordance with one or more illustrative embodiments.

For the interdental gap detection steps, a weighting process by a weighting module 316 weights the potential interdental gaps, based on one or more of the interdental gap detection steps, to obtain one or more delimiters. For example, after finding the gaps 802 and minima 804, their features are characterized and assigned weights based on one or more factors such as their geometric attributes. As shown in FIG. 9A, the gaps and minima are representative of fixed interdental gaps 902 or potential interdental gaps 904, with potential interdental gaps 904 having a lower degree of certainty (e.g. 20-60.99% confidence level) than fixed interdental gaps 902 which have high (e.g. 95-100% or 61-100%) degree of certainty, e.g. due to a plurality of lingual and buccal gaps or minima being in agreement. The fixed interdental gap 902 and potential interdental gap 904 are referred to herein as fixed delimiters and potential delimiters and are further described hereinafter.

For the potential delimiter candidates from the interdental gap detection steps: cross sections process using the cross-sections module 302, gingiva margin process using the interdental papilla detection module 312 and/or the tooth intervals/regions process using the classification module 314, weights are supported, which rate the probability that a given delimiter candidate is at the correct position and thus is an actual delimiter or interdental gap. These delimiter candidates are compared to each other and based on some heuristics or defined comparison algorithm, which are configured to handle preparations, unified delimiters are determined. Unified delimiters may, for example, represent delimiters within a defined area or delimiters having certainty above at least a threshold degree of certainty (e.g. >60%) Thus, a fixed delimiter may describe a position, where the various gaps or minima from lingual and/or buccal sources are in agreement and a potential delimiter may describe a position with a certain uncertainty that may be stored as a weight. Alternatively, fixed delimiters may have the highest weight and potential delimiters have comparatively lower weights. Of course, these examples are not meant to be limiting as other examples, processes and algorithms may be achieved in light of the descriptions.

Figure 9B:
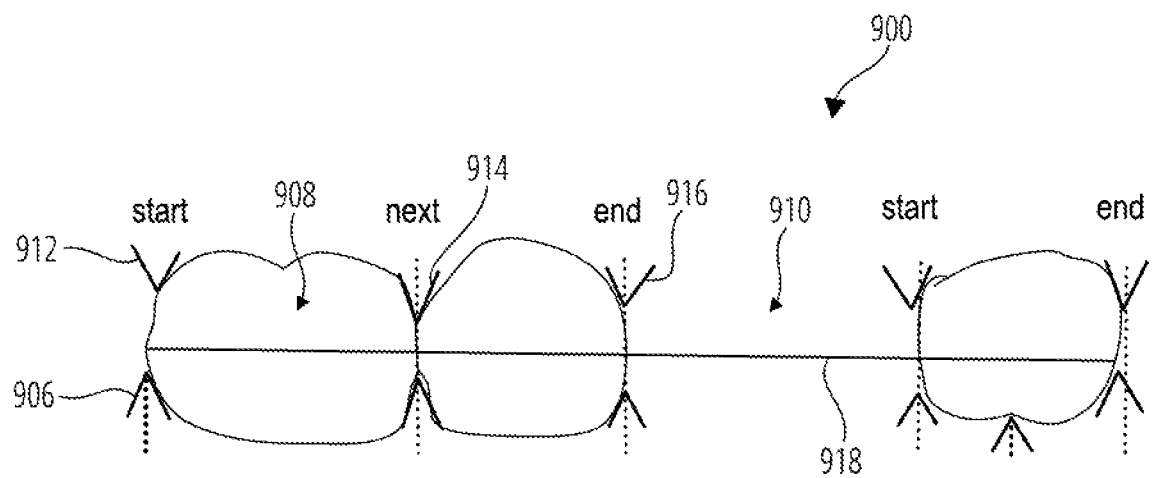
FIG. 9B depicts a 2D representation of a jaw in accordance with one or more illustrative embodiments.

With reference to FIG. 9B, one or more delimiters 906 are shown along a common reference line 918 in a 2D view of a combined delimiter arrangement 900. The one or more delimiters 906 are delimiters obtained from the various interdental gap detection steps and combined on a common reference line 918. The one or more delimiters may also have respective weights associated with them. By using a reference line or curve in each interdental gap detection step that can be easily located, such as the spline curve 502 or a curve or line that has a defined spatial relationship with the spline curve 502 or other common curve, the delimiters 906 from each of the interdental gap detection steps can be aligned on the common reference line 918 of FIG. 9B for further analyses. Of course, the common reference line 918 or curve can itself be the spline curve 502 or a straightened spline curve.

In step 408, tooth number probabilities are proposed for each of one or more possible tooth alignments between one or more pairs of fixed delimiters (i.e. tooth number probabilities are proposed for each possible combination of intervals between fixed delimiters), using an alignments module 318. The alignments module 318 is a machine learning engine having a machine learning model that is trained to predict the probabilities based on a large training dataset. More specifically, tooth number probabilities are automatically proposed, for each of one or more possible tooth alignments between adjacent fixed delimiters, using the alignments module 318. There may be a number of possible teeth between two fixed delimiters, for example, one or two teeth may fit in the space between two adjacent fixed delimiters. Further, there may be a plurality of adjacent pairs of fixed delimiters. In between each pair of fixed delimiters, there may also be potential delimiters with associated uncertainty, such that in some cases, more than one possible tooth/tooth alignment can fit in between each pair of fixed delimiters, whereas in other cases only one possible tooth/tooth alignment fits in between said pair of fixed delimiters. Each possible tooth that fits wholly or partially into the space between said two delimiters is a tooth alignment. By looping or cycling through all possible teeth alignments that can fit wholly or partially in said space, and repeating for all pairs of adjacent fixed delimiters, a probability that said tooth corresponds to any of the tooth numbers of a dental cavity is predicted by the alignments module. In an embodiment, the alignments module 318 is a machine learning engine. By sequentially providing the alignments module with all possible tooth alignments for within at least one pair of fixed delimiters, a set of tooth number probabilities for each possible tooth alignment is predicted. The set represents all possible tooth types. For example, since there are thirty-two teeth in an adult dental cavity, with the dental cavity having four similar quadrants, there may be a total of eight possible tooth numbers. Thus, in an embodiment, for each possible tooth alignment, the alignments module returns 8 tooth number probabilities ($P_{pta-t1}$, $P_{pta-t2}$, ... $P_{pta-t8}$) where "$P_{pta-tN}$" represents the probability that a current possible tooth alignment is tooth number N. Of course, this is not limiting as any suitable manifestation of these and other similar artifacts can be selected within the scope of the illustrative embodiments. For example, a different number of probabilities or a different processing of input data may be obtained in light of the illustrative embodiments. A process 1200 of the machine learning model is described in FIG. 12 wherein for each of the one or more possible tooth alignments the following steps are performed. In step 1202, a preprocessing step is performed by constructing an estimated model representative of the current possible tooth alignments between two fixed delimiters. In step 1204, the constructed estimated model is provided as input to the machine learning model, the machine learning model being a trained machine learning model. In step 1206, the tooth number probabilities of the current possible tooth alignment are obtained as output.

Figure 13:
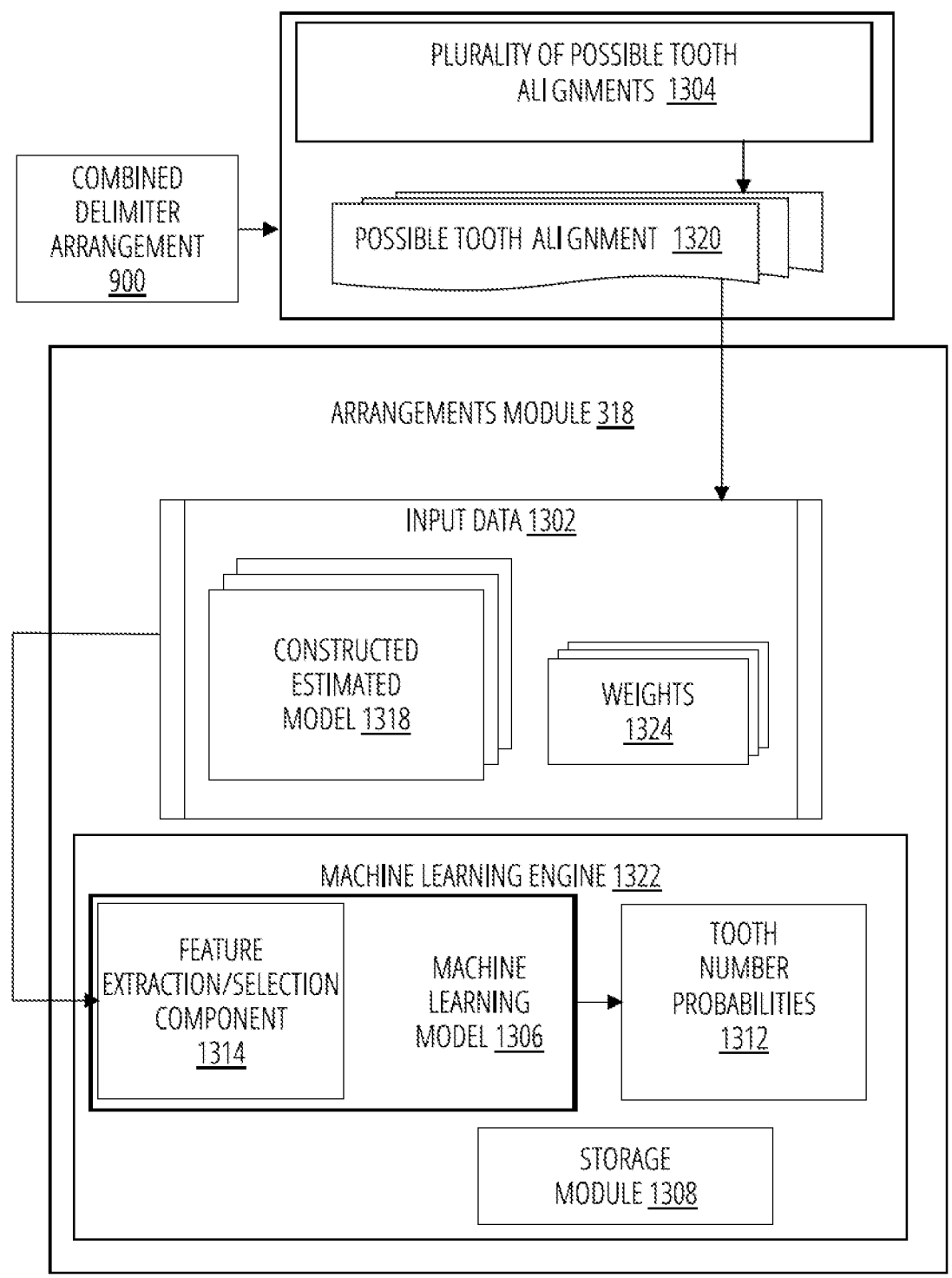
FIG. 13 depicts an alignments module in accordance with one or more illustrative embodiments.

With reference to FIG. 13, this figure depicts a block diagram of an example configuration for proposal of tooth number probabilities 1312 in accordance with an illustrative embodiment. Alignments module 318 is a component of any of server applications 116 or client application 120 in FIG. 1, depending on the particular implementation.

Briefly, a 2D-Array of height values representative of a geometry of tooth alignment are input to a M/L model which determines by ML probabilities that each possible tooth number would fit on this geometry. This classification is applied for all meaningful intervals or alignments between delimiters independently of the global optimization. Due to a usual large number of fixed delimiters there may not be so many intervals representative of potential delimiters which have to be analyzed, leaving mainly large intervals between fixed pairs of delimiters with no other delimiters in between (typically representative of one possible tooth) and areas with ambiguous uncertain/potential delimiters (typically representative of more than one possible tooth). Thereafter, by, for example, a dynamic programming approach which takes into account probabilities computed so far, the "plurality of possible tooth alignments" are analyzed wherein for every tooth number, estimations for minimum, average and maximum widths are also considered.

Figure 14:
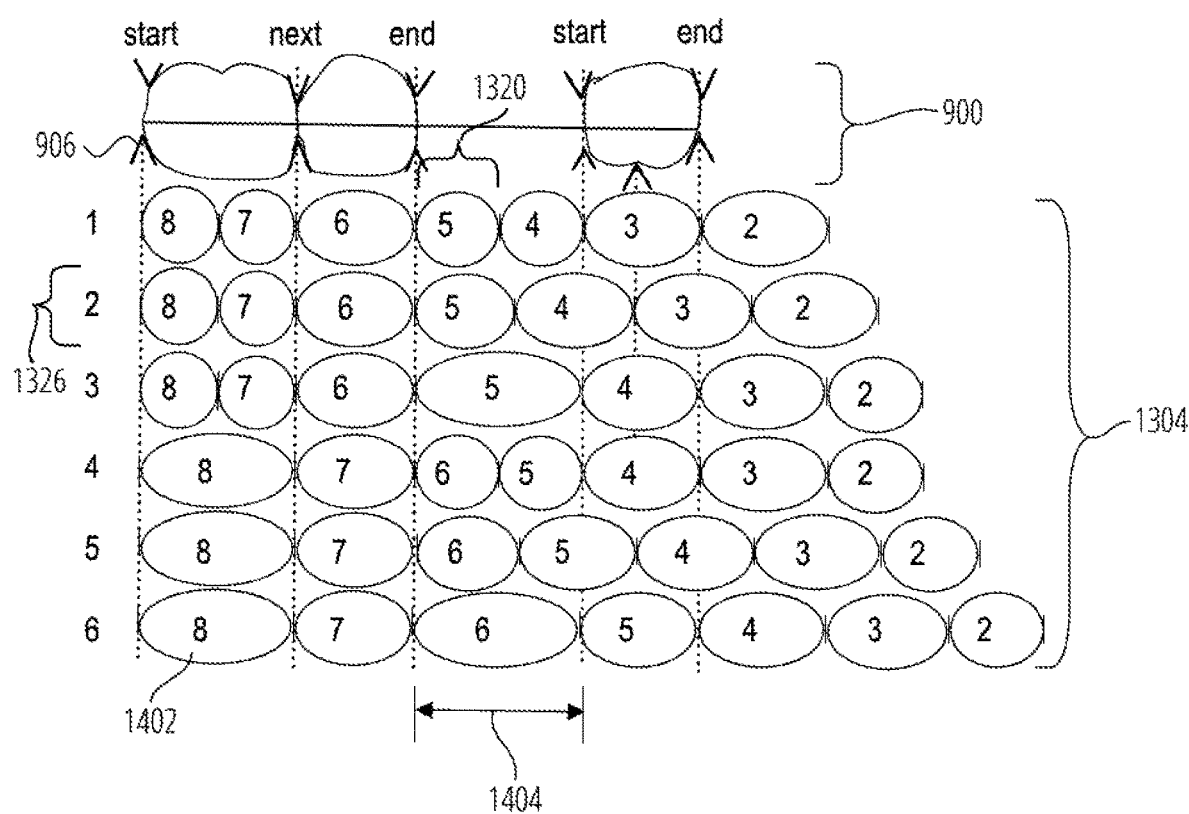
FIG. 14 depicts a 2D representation of a jaw in accordance with one or more illustrative embodiments.

More specifically, alignments module 318 may sequentially obtain a possible tooth alignment 1320 from a plurality of possible tooth alignments 1304 which are based on the combined delimiter arrangement 900. A 2D representation of the plurality of possible tooth alignments 1304 is shown in FIG. 14, wherein a possible tooth alignment 1320 of the plurality of possible tooth alignments 1304 represents a possible arrangement of a tooth about positions represented by the delimiters 906, and more specifically, the possible disposition of a tooth in the space between two chosen or adjacent fixed delimiter. See FIG. 14, which is representative of the first seven possible teeth 1402 of an illustrative jaw (numbered 2 to 8 in the ovals of FIG. 14) with the remaining possible teeth being truncated solely for illustrative purposes. Six possible alignment arrangements 1326 (numbered 1 to 6) are shown solely for illustrative purposes. It is possible that any number of alignment arrangements 1326 needed to account for all possible tooth alignments of the eight teeth in a quadrant or even for all thirty-two possible teeth of a patient's dental cavity about the delimiters 906 may be analyzed at the same time by the machine learning model for automating the administration phase and restoration generation process. Thereafter, a global optimization module may compute the optimal arrangement by dynamic programing to reduce the number of arrangements that have to be considered. Turning back to FIG. 13, for each possible tooth alignment 1320, a constructed estimated model 1318 (e.g. from a database of generalized models) is created, using the preprocessing module 320, for use as input to the machine learning engine 1322. The constructed estimated model 1318 may be a 2.5D estimated model representative of, or constructed using, a 2D view of the possible alignment 1320. The 2.5D model may be represented as a 2D array of height values that correspond to heights (relative to a plane parallel to the occlusal plane) of a plurality surface points of the estimated model. However this is not meant to be limiting as other formats can be used in light of the specification, including for example, a vector representative of estimated teeth, pixels of a 2D image, 2.5 D images having depth information and gray level information, 3D points of 3D images of estimated/generalized teeth etc. In an illustrative embodiment probabilities may be generated for each possible tooth 1402. The illustrative embodiments are thus not meant to be limiting and variations obtainable in light of the descriptions herein, such as output probabilities of preparation types, are meant to be included. Thus, for all possible alignments of teeth between the potential and fixed delimiters, the tooth number or preparation types are now determined with the help of neural networks. An example neural network for the machine learning model 1306 is a CNN or a PointCNN (Point Convolutional Neural Network), which is generalization of typical CNNs (Convolutional Neural Network) to learn features from point clouds.

In the case of a CNN, it is a feed-forward artificial neural network which in a classic form consists of a convolutional layer, followed by a pooling layer. The CNN learns by learning free parameters or classifiers of the convolution kernel per layer and their weighting when calculating the next layer. A training of the machine learning model 1306 according to an illustrative embodiment is discussed hereinafter.

In another embodiment, feature extraction/selection component 1314 is configured to generate relevant features for a proposal based on data from all the different available inputs (e.g., weights 1324). In the embodiment, feature extraction/selection component 1314 receives a request which includes at least an identification of output type needed. Based on the type, feature extraction/selection component 1314 obtains any combination of specific input data that are relevant to the request or proposal needed. However, in most embodiments, feature extraction is incorporated in the deep neural network or the machine learning model 1306 and feature selection, if any, may be carried out outside the machine learning model.

In an illustrative embodiment, storage module 1308 stores the output of machine learning model 1306 which are probabilities or likelihood evaluations or even classifications of the tooth number of each of one or more possible teeth 1402, or probabilities or likelihood evaluations or even classifications of the possible tooth alignment 1320.

In an illustrative embodiment, after producing output evaluations, the alignments module 318 or an application 120 of the alignments module 318 may perform additional operations automatically or in response to a request.

Figure 15:
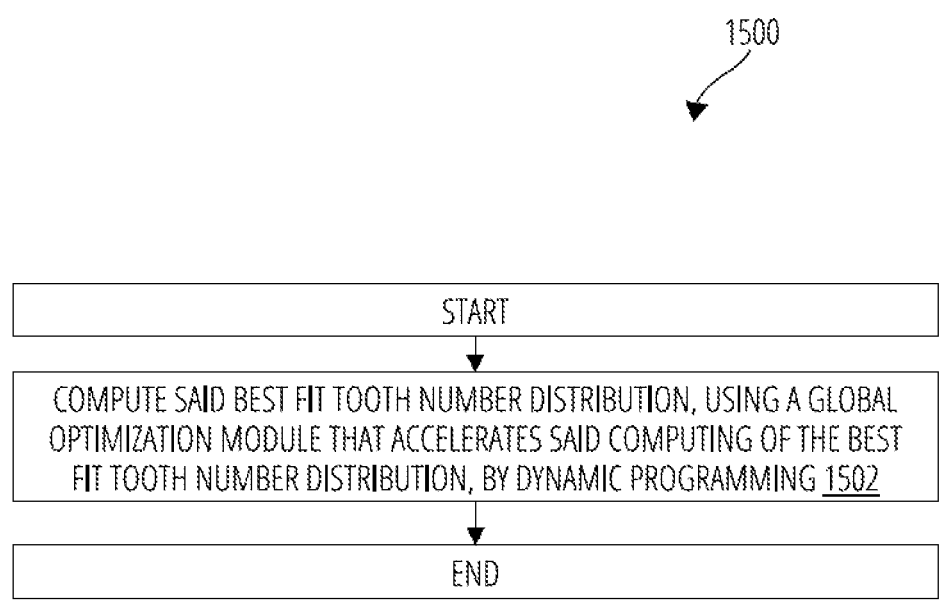
FIG. 15 depicts a process in accordance with one or more illustrative embodiments.
Figure 16:
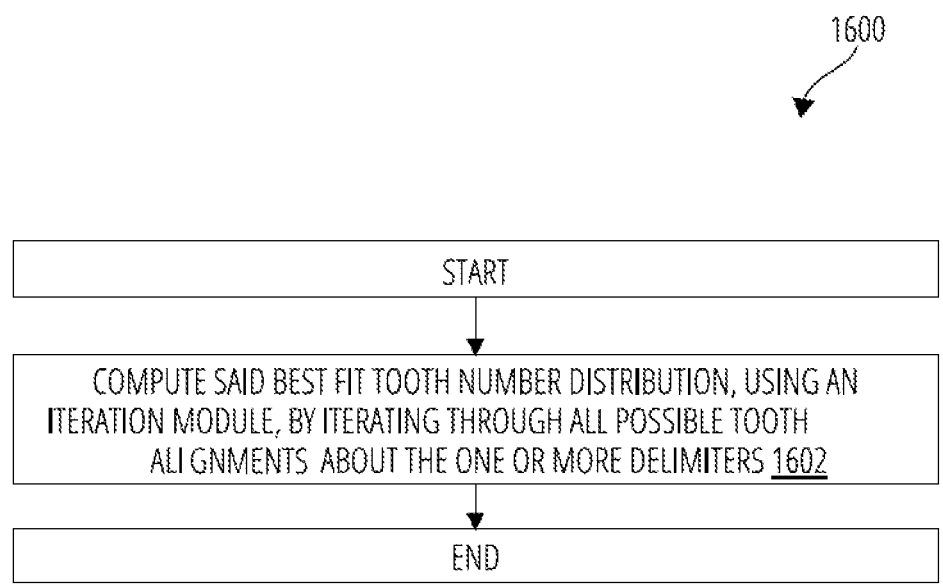
FIG. 16 depicts a process in accordance with one or more illustrative embodiments.
Figure 17:
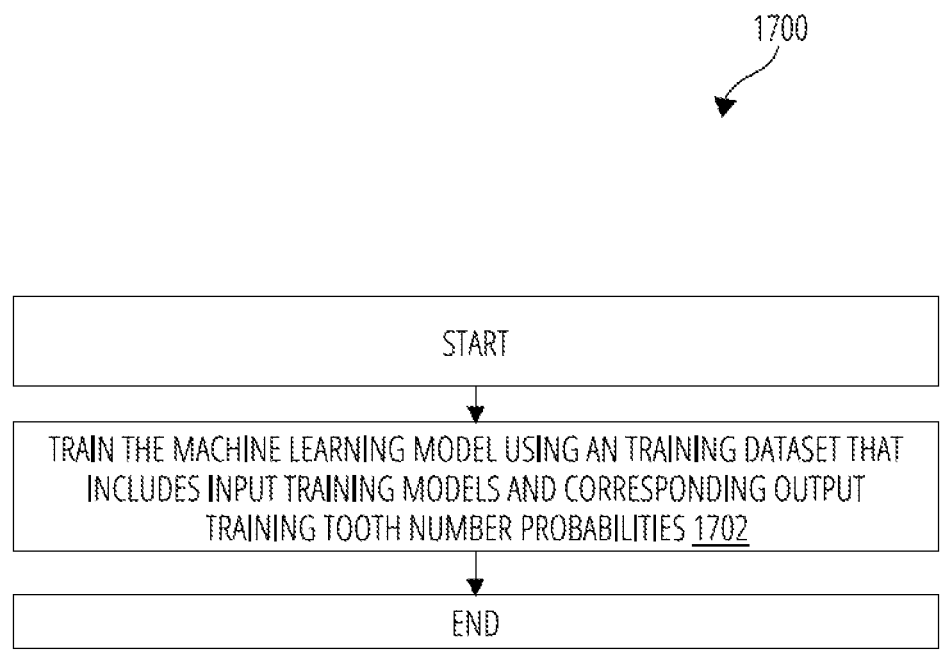
FIG. 17 depicts a process in accordance with one or more illustrative embodiments.

Further, the best fit computation module 324 computes a best fit tooth number distribution or arrangement according to a defined criteria (e.g. the most probable of the possible tooth alignments 1320) using at least the proposed tooth number probabilities 1312 or evaluations. To save time, the best fit tooth number distribution may be computed in a global optimization process, as shown in FIG. 15, using the global optimization module 326 which accelerates said computing of the best fit tooth number distribution, by dynamic programming. This ensures that the optimal solution is reached without a need to iterate through all possibilities. Thus, the most globally probable sequence of teeth around/between interdental gaps is calculated by dynamically programming which involves using a recursive approach by memorizing trends in subproblem solutions. This typically reduces time complexities from exponential to polynomial. In this step, in addition to the classifications by the neural network and the availability of mean tooth widths, the probability distribution of the occlusal opposing teeth may also taken into account in finding the best fit tooth number distribution. The global optimization may result in the segmentation of the jaw into tooth intervals 1404 for each tooth number, which tooth intervals may be used in further computations.

Alternatively, the best fit tooth number distribution may be computed iteratively, albeit slower that the global optimization, by iterating through the probabilities of all possible tooth alignments 1320 (FIG. 16) for all possible arrangements of alignments 1326.

In addition to detecting the possible teeth, preparations in the 3D model 504 may also be detected. Herein a 3D surface based neural network similar to the machine learning model 1306, automatically detects for each tooth interval 1404 if a tooth exists and if this tooth is an unprepared tooth or a prepared tooth. The type of preparation may also be determined for each tooth interval 1404 that is classified as a preparation using a similar machine learning algorithm.

Further, scanbodies and their implant axis may be detected beforehand by a separate algorithm such as a curve detection algorithm and assigned to a tooth interval 1404. Different types of scanbodies are defined by how the individual base geometries building the scanbody are arranged in relation to each other. First, similarly curved regions are detected on the entire 3D model geometry and then matching geometric primitives are inserted into the regions.

Further, if preparations are found in direct neighborhood of tooth intervals 1404 that are toothless, the most probable combination of poetics and crowns to a bridge may be automatically proposed using known algorithms.

Even further, for each preparation found, the preparation border may be calculated automatically based on known algorithms. For each preparation found, a patient-specific restoration is calculated automatically based on a restoration generation algorithm after having automatically determined the insertion axis for the restoration. The restoration generation algorithm, in an illustrative embodiment, analyzes the individual patient's occlusion and the anatomy of the adjacent teeth, based on e.g. the scanned 3D model 504, so that the restoration can be designed to be patient specific.

The machine learning model 1306 may be trained using a training dataset as described herein. In step 1702, of FIG. 17, the machine learning model may be trained using a training dataset that includes input training models and corresponding output training tooth number probabilities.

Figure 18:
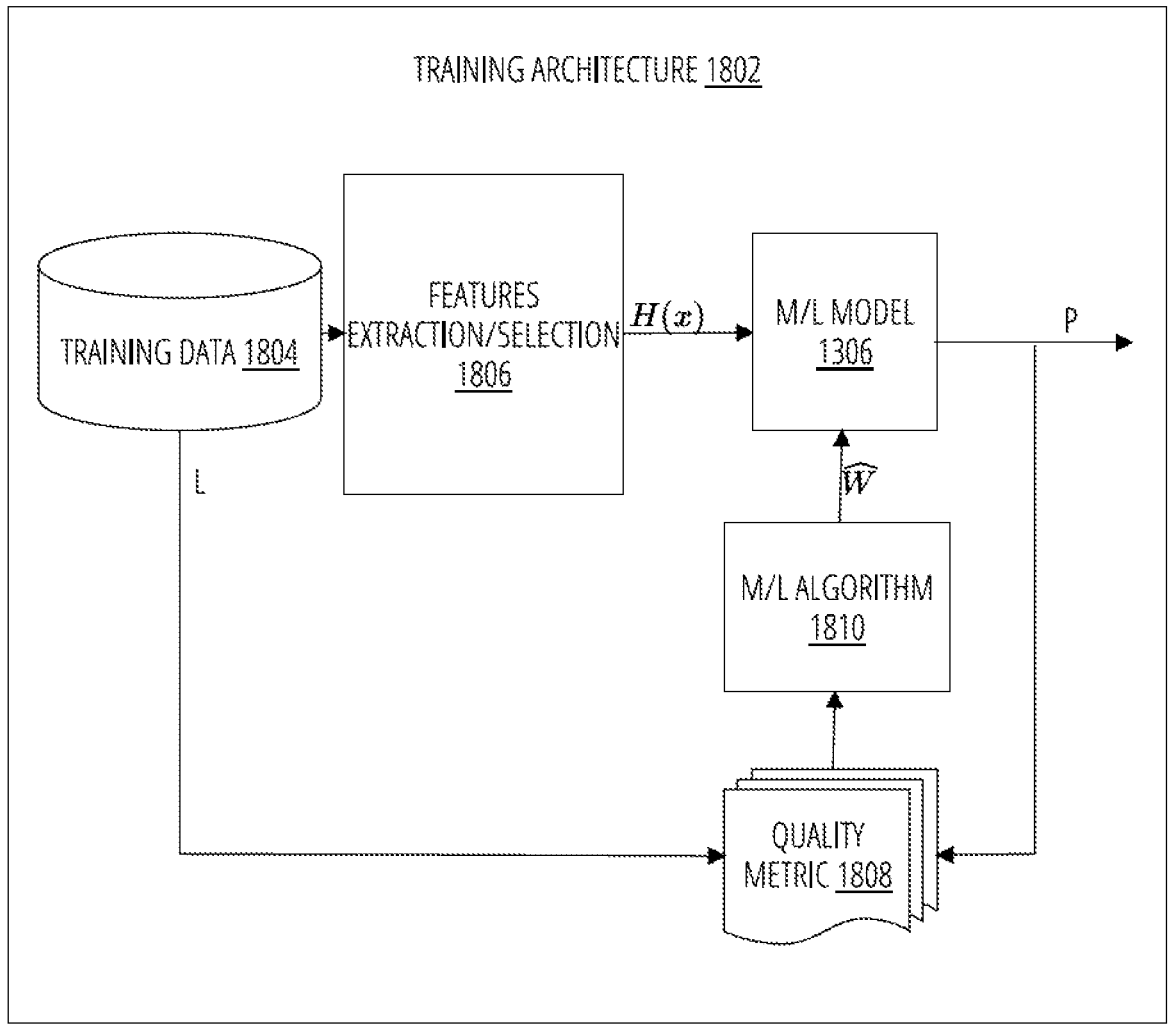
FIG. 18 depicts a training architecture in accordance with one or more illustrative embodiments.

FIG. 18 shows a training architecture 1802 for training the machine learning model 1306. The machine learning model 1306 is trained using various types of training data 1804 including sample constructed estimated models constructed using sample possible tooth alignments. The samples may be based on real patient data from a database. The training data 1804 may also include weights of the delimiters that correspond to a confidence level of the tooth types in the constructed estimated model or of the tooth intervals. In an embodiment, upon receiving a request to provide a recommendation, the application creates an array of values that are input to the input neurons of the machine learning model 1306 to produce an array that contains the tooth number probabilities. As shown in FIG. 18, program code in some embodiments optionally extracts or selects various features/attributes 1806 from training data 1804 with the training data entries having labels L. In the case of feature extraction, it may be incorporated in the machine learning model 1306 itself. The features are utilized to develop a predictor function, H(x) or a hypothesis, which the program code utilizes as a machine learning model 1306. In identifying various features/attributes in the training data 1804, the program code may utilize various techniques including, but not limited to, mutual information, which is an example of a method that can be utilized to identify features in an embodiment. Other embodiments may utilize varying techniques to select features, including but not limited to, principal component analysis, diffusion mapping, a Random Forest, and/or recursive feature elimination (a brute force approach to selecting features), to select the features. "P" is the output (e.g., tooth number probabilities or evaluations or classifications) that can be obtained, which when received, could further trigger the dental restoration system 300 to perform other steps such as find a best fit tooth number distribution. The program code may utilize a machine learning algorithm 1810 to train machine learning model 1306, including providing weights for the outputs, so that the program code can prioritize various changes based on the predictor functions that comprise the machine learning model 1306. The output can be evaluated by a quality metric 1808.

By selecting a diverse set of training data 1804, the program code trains machine learning model 1306 to identify and weight various attributes of patients' teeth. To utilize the machine learning model 1306, the program code obtains (or derives) input data or features to generate an array of values to input into input neurons of a neural network. Responsive to these inputs, the output neurons of the neural network produce an array that includes the tooth number probabilities 1312 to be stored and/or evaluated contemporaneously.

Figure 19:
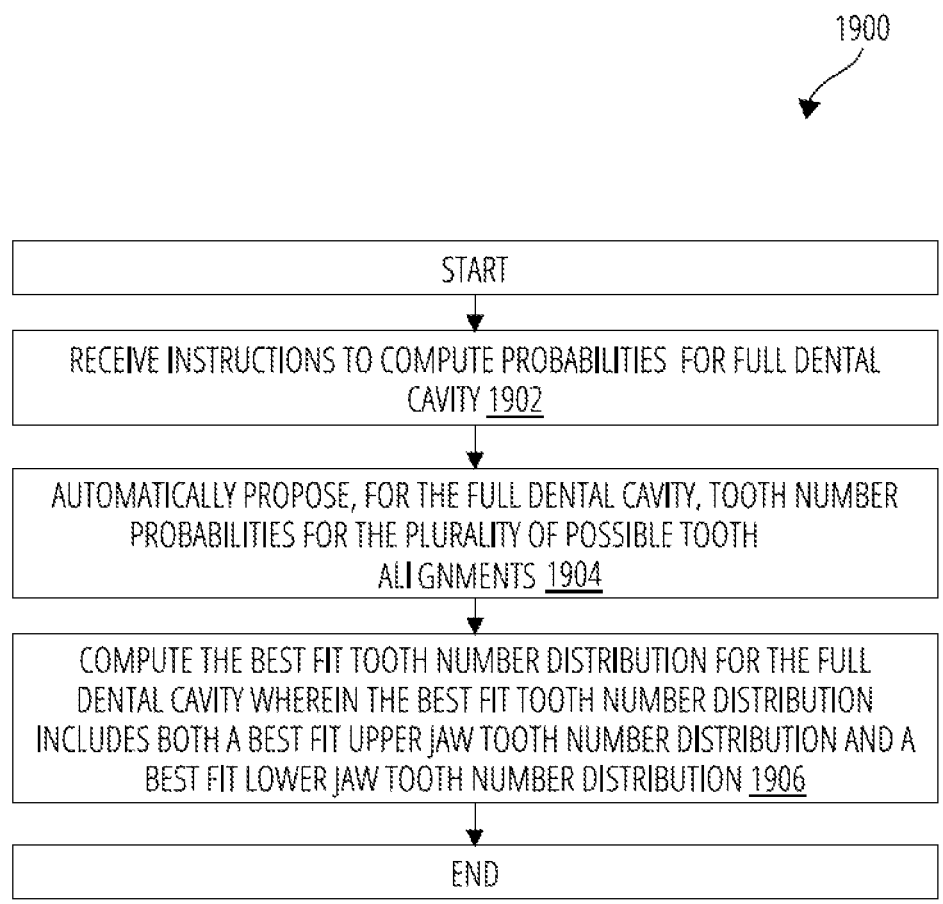
FIG. 19 depicts process in accordance with one or more illustrative embodiments.

While the constructed estimated model 1318 may be constructed for any number of teeth, in an illustrative model, the constructed estimated model 1318 may be constructed for all teeth of the upper and lower jaw as shown in process 1900 of FIG. 19. In step 1902, process 1900 receives instructions to compute probabilities for the full upper jaw. In step 1904, process 1900 automatically proposes, for the full dental cavity, tooth number probabilities for the plurality of possible tooth alignments. In step 1906, process 1900 computes the best fit tooth number distribution for the full dental cavity wherein the best fit tooth number distribution includes both a best fit upper jaw tooth number distribution and a best fit lower jaw tooth number distribution. The process 1900 ends afterwards and another process may begin to create a restoration based on the best fit tooth number distribution.

Figure 20A:
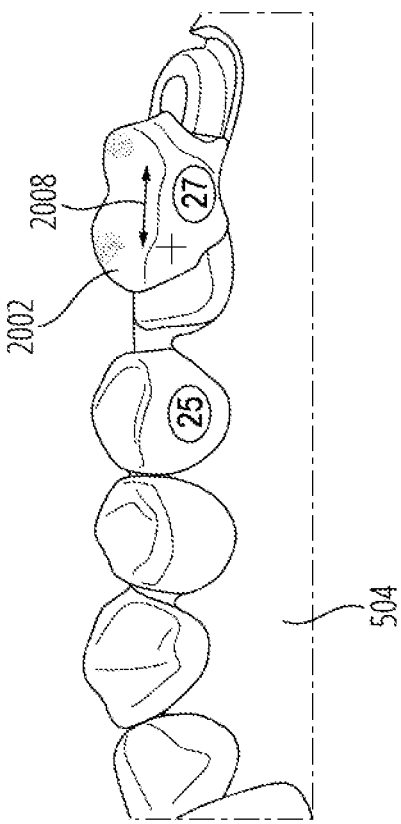
FIG. 20A depicts a 3D model having a restoration in accordance with one or more illustrative embodiments.
Figure 20B:
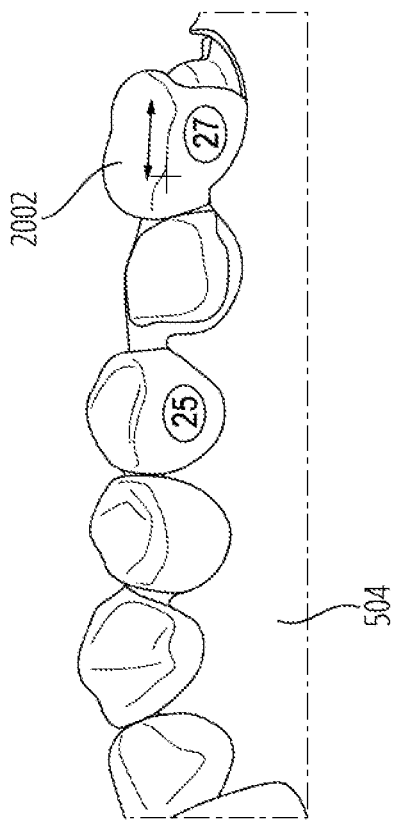
FIG. 20B depicts a 3D model having a restoration in accordance with one or more illustrative embodiments.
Figure 20C:
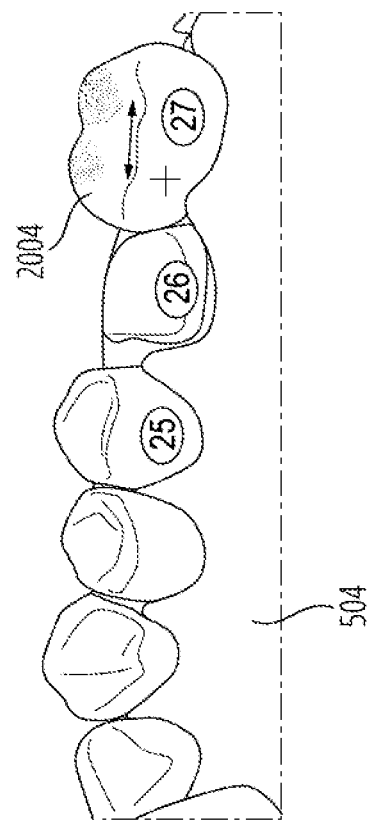
FIG. 20C depicts a 3D model having a restoration in accordance with one or more illustrative embodiments.

The restoration system 300 may further provide tools for correcting wrong tooth positions and for intuitive fine adjustment of the dental cavity. As shown in FIG. 20A-FIG. 20D, for the rare case of an incorrectly positioned first restoration 2002, the drag and drop tool 2008 tool is used for corrections. The drag and drop tool 2008 may be adapted for different display types, including touchscreens, and may be operated from all viewing directions. Each restoration such as a first restoration 2002 can be moved along the jaw as shown in FIG. 20A-FIG. 20B. By selecting the first restoration 2002 and releasing it at a new position as shown in FIG. 20C, a second restoration 2004 may be recalculated for the new position (See FIG. 20C). The recalculation may be based on one or more of the processes described herein. For example, a high degree of confidence may be afforded to a different tooth interval 1404 or a restoration may be directly calculated at the new position using known algorithms.

Figure 20D:
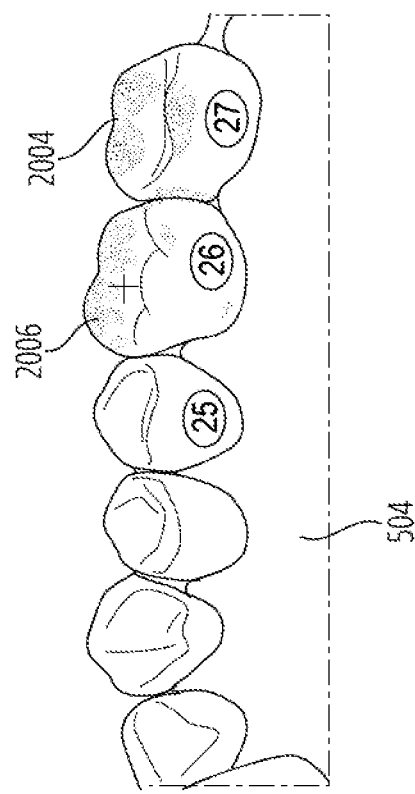
FIG. 20D depicts a 3D model having a restoration in accordance with one or more illustrative embodiments.

By double clicking or double touching a position of a preparation, a recalculated first restoration 2006 is added and correctly fitted into the gap, See FIG. 20D. Further, by double clicking or double touching a restoration the restoration may be removed.

Figure 21A:
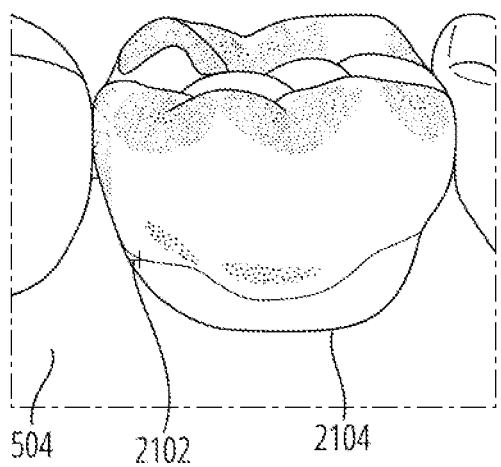
FIG. 21A depicts a 3D model having a restoration in accordance with one or more illustrative embodiments.
Figure 21B:
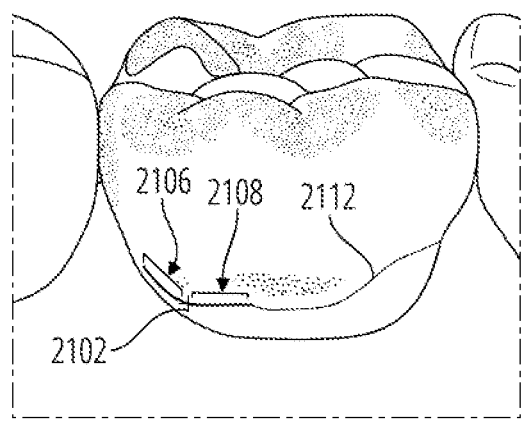
FIG. 21B depicts a 3D model having a restoration in accordance with one or more illustrative embodiments.
Figure 21C:
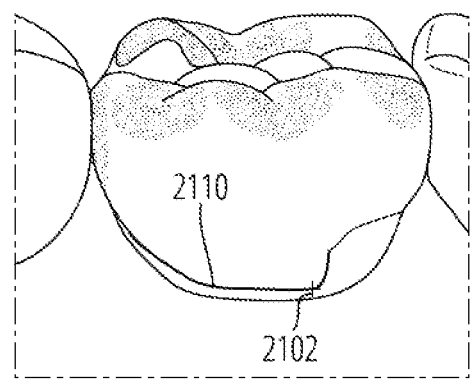
FIG. 21C depicts a 3D model having a restoration in accordance with one or more illustrative embodiments.
Figure 21D:
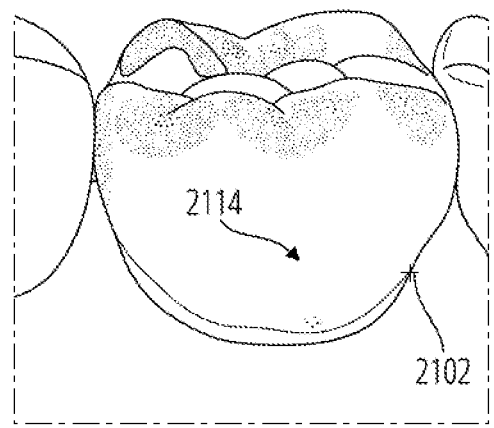
FIG. 21D depicts a 3D model having a restoration in accordance with one or more illustrative embodiments.

The restoration system 300 may further provide an intuitive tool for fine adjustment of certain cavity regions as shown in FIG. 21A-FIG. 21D. In FIG. 21A, a cursor 2102 is positioned onto the preparation margin and a control, e.g. left mouse button is pressed. In FIG. 21B, the cursor is moved along a desired new margin line 2104 with the mouse button still pressed. As shown in FIG. 21B, in an area behind 2106 the cursor 2102 jumps to the most probable alternative course of the restoration margin detected by one or more of the automation algorithms described herein. In an area in front 2108 of the cursor 2102, a smooth adaptation of the new border to the previous restoration margin 2112 is computed, the length of which may depend on the distance of the current cursor position to the previous restoration margin 2112. As shown in FIG. 21C, by short release of a control, e.g. the left mouse button, in the area behind 2106 the cursor 2102 position is fixed, by right click of the mouse button the fixations may be canceled. The surface of the restoration 2114 is contemporaneously adapted to the new restoration margin line 2110 as shown in FIG. 21D. When corrected line meets the existing restoration margin, the adaption of the restoration may stop. The described interaction may also be performed in a similar manner by touch control wherein, starting with the finger on the existing preparation margin, the new preparation margin is followed. When the finger is shortly released, the already covered sections of the new line will be fixated. If the existing preparation margin is crossed, the interaction is stopped. To make a correction of the restoration margin simpler, the restoration surface may be switched to be transparent in a certain region when moving the cursor inside the restoration.

Thus, a computer implemented method, system or apparatus, and computer program product are provided in the illustrative embodiments for automating the tooth administration phase such as all tooth manual management processes of a restoration workflow and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, including but not limited to computer-readable storage devices as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method comprising:
   forming a spline along a jaw;
   proposing potential interdental gaps, by performing one or more of the interdental gap detection steps of: analyzing tooth cross-sections, detecting interdental papilla, and classifying tooth intervals;
   weighting the potential interdental gaps, based on one or more of the interdental gap detection steps, to obtain one or more delimiters;
   automatically proposing a tooth number probability, for each of one or more possible tooth alignments between at least one pair of fixed delimiters of the one or more delimiters, using an alignments module; and
   computing a best fit tooth number distribution, from the one or more possible tooth alignments, responsive to the automatically proposing step, using at least the proposed tooth number probability of each of the one or more possible tooth alignments;
   wherein the alignments module is a machine learning engine.

2. The computer-implemented method of claim 1, wherein a patient-specific restoration is generated based on the computed best fit tooth number distribution.

3. The computer-implemented method of claim 2, wherein another patient-specific restoration is regenerated, responsive to the generation of the patient-specific restoration being incorrect, based on a selection of a new tooth position for the another patient-specific restoration.

4. The computer-implemented method of claim 2, wherein an incorrect margin of the patient-specific restoration is corrected by adjusting said incorrect margin to a new position based on a probable margin course.

5. The computer-implemented method of claim 1, wherein the interdental gap detection steps are all performed and are performed in parallel.

6. The computer-implemented method of claim 1, further comprising:
   computing said best fit tooth number distribution, using a global optimization, which accelerates said computing of the best fit tooth number distribution, by dynamic programming.

7. The computer-implemented method of claim 6, wherein the global optimization uses as input, one or more factors selected from the list consisting of a correspondence between an upper and a lower jaw, sizes of teeth, weights from the weighting step, and an output of the machine learning engine.

8. The computer-implemented method of claim 1, further comprising
   computing said best fit tooth number distribution, by iterating through all possible tooth alignments about the one or more delimiters.

9. The method of claim 1, wherein the best fit tooth number distribution is computed for a full dental cavity that includes an upper jaw and a lower jaw, wherein a plurality of delimiters are obtained and a plurality of possible tooth alignments between said at least one pair of fixed delimiters are determined for both the upper jaw and the lower jaw.

10. The computer-implemented method of claim 9, further comprising:
    automatically proposing, for the full dental cavity, tooth number probabilities for the plurality of possible tooth alignments, and
    computing the best fit tooth number distribution for the full dental cavity, the best fit tooth number distribution includes both a best fit upper jaw tooth number distribution and a best fit lower jaw tooth number distribution.

11. The computer-implemented method of claim 1, wherein in the computing step, the best fit tooth number distribution is computed for one jaw, and wherein another best fit tooth number distribution is inferred for an opposing jaw based on the computed best fit tooth number distribution.

12. The computer-implemented method of claim 1, wherein in the computation step, the best fit tooth number distribution is computed for a portion of one jaw.

13. The computer-implemented method of claim 12, wherein another best fit tooth number distribution is inferred for an opposing portion of the jaw or for an opposing portion of an opposing jaw based on the computed best fit tooth number distribution.

14. The computer-implemented method of claim 12, wherein the portion of one jaw includes eight possible teeth of a first quadrant of a jaw.

15. The computer-implemented method of claim 1, wherein the forming step is automatic.

16. The computer-implemented method of claim 1, wherein the one or more delimiters are determined to be potential and/or said fixed delimiters based on their respective weights.

17. The computer-implemented method of claim 1, further comprising automatically proposing at least one tooth preparation type probability between said at least one pair of fixed delimiters.

18. The computer-implemented method of claim 1, wherein at least one of the one or more delimiters indicates a space that is representative of one or more missing teeth.

19. The computer-implemented method of claim 1, wherein a space between two delimiters that are above a threshold distance apart, is representative of one or more possible teeth.

20. The computer-implemented method of claim 19, wherein the automatically proposing step predicts a tooth number of said one or more possible teeth that fits inside said space.

21. The computer-implemented method of claim 1, wherein at least one of the one or more delimiters indicates a boundary between adjacent teeth.

22. The computer-implemented method of claim 1, wherein the tooth number probability is a percentage or value between 0 and 1.

23. The computer-implemented method of claim 1, wherein the tooth number probability is a likelihood evaluation or classification.

24. The computer-implemented method of claim 1, wherein the machine learning engine has a model that is based on 3D surface based neural network.

25. The computer-implemented method of claim 1, further comprising:
for each of the one or more possible tooth alignments:
performing a preprocessing step by constructing an estimated model representative of a current possible tooth alignment;
providing the constructed estimated model as input to the machine learning model;
and obtaining, as output, the tooth number probability.

26. The computer-implemented method of claim 25, wherein the estimated model is represented as a 2D array of height values that correspond to heights of a plurality of surface points of a model.

27. The computer-implemented method of claim 25, wherein the constructed estimated model is a 3D model.

28. The computer-implemented method of claim 1, further comprising:
training the machine learning model using a training dataset that includes input training models and corresponding output training tooth number probabilities.

29. The computer-implemented method of claim 28, wherein a space in an input training model is interpreted as corresponding to one or two missing teeth that correspond respectively to one or two same or distinct tooth numbers.

30. A computing system comprising:
a processor; and
a memory storing instructions that, when executed by the processor, configure the system to:
form a spline along a jaw;
propose potential interdental gaps by performing one or more of the interdental gap detection steps of: analyzing tooth cross-sections, detecting interdental papilla, and classifying tooth intervals;
weight the potential interdental gaps, based on one or more of the interdental gap detection steps, to obtain one or more delimiters;
automatically propose a tooth number probability, for each of one or more possible tooth alignments between at least one pair of fixed delimiters of the one or more delimiters, using an alignments module; and
compute a best fit tooth number distribution, from the one or more possible alignments, responsive to the automatically proposing step, using at least the proposed tooth number probability of each of the one or more possible tooth alignments;
wherein the alignments module is a machine learning engine.

31. The computing system of claim 30, wherein a patient-specific restoration is generated based on the computed best fit tooth number distribution.

32. The computing system of claim 30, wherein the machine learning engine has a model that is based on a 3D surface based neural network.

33. A non-transitory computer-readable storage medium storing instructions that when executed by a computer, cause the computer to:
form a spline along a jaw;
propose potential interdental gaps by performing one or more of the interdental gap detection steps of: analyzing tooth cross-sections, detecting interdental papilla, and classifying tooth intervals;
weight the potential interdental gaps, based on one or more of the interdental gap detection steps, to obtain one or more delimiters;
automatically propose a tooth number probability, for each of one or more possible tooth alignments between at least one pair of fixed delimiters of the one or more delimiters, using an alignments module; and
compute a best fit tooth number distribution, from the one or more possible alignments, responsive to the automatically proposing step, using at least the proposed tooth number probability of each of the one or more possible tooth alignments;
wherein the alignments module is a machine learning engine.

* * * * *